(12) United States Patent
Dehmlow et al.

(10) Patent No.: US 9,090,565 B2
(45) Date of Patent: Jul. 28, 2015

(54) 1-PYRIDAZINYL-HYDROXYIMINO-3-PHENYL-PROPANES

(71) Applicant: Hoffmann-La Roche Inc., Nutley, NJ (US)

(72) Inventors: Henrietta Dehmlow, Loerrach (DE); Rainer E. Martin, Basel (CH); Patrizio Mattei, Riehen (CH); Ulrike Obst Sander, Reinach BL (CH); Hans Richter, Grenzach-Wyhlen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 97 days.

(21) Appl. No.: 13/675,007

(22) Filed: Nov. 13, 2012

(65) Prior Publication Data
US 2013/0123267 A1 May 16, 2013

(30) Foreign Application Priority Data

Nov. 14, 2011 (EP) .................................. 11188959

(51) Int. Cl.
 *C07D 237/08* (2006.01)
 *C07D 401/10* (2006.01)
 *C07D 237/14* (2006.01)

(52) U.S. Cl.
 CPC ............ *C07D 237/08* (2013.01); *C07D 237/14* (2013.01); *C07D 401/10* (2013.01)

(58) Field of Classification Search
 CPC ... C07D 237/08; C07D 237/14; C07D 401/10
 USPC .................................. 544/238, 239, 240, 241
 See application file for complete search history.

(56) References Cited

FOREIGN PATENT DOCUMENTS

| WO | 2007/147879 | 12/2007 |
|----|-------------|---------|
| WO | 2008/003611 | 1/2008  |
| WO | 2008/097976 | 8/2008  |

OTHER PUBLICATIONS

Keitel et al., "Hepatology" 50(3):861-870 (2009).
Pellicciari et al., "Journal of Medicinal Chemistry" 52(24):7958-7961 (2009).
Katsuma et al., "Biochem. Biophys. Res. Commun." 329(1):386-390 (2005).
International Search Report for PCT/EP2012/072348 dated Jan. 18, 2013.

*Primary Examiner* — Alexander R Pagano

(57) ABSTRACT

This invention relates to 1-pyridazinyl-hydroxyimino-3-phenyl-propanes of the formula

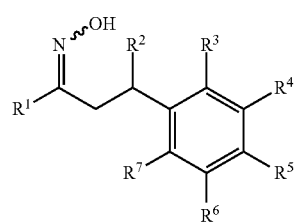

wherein $R^1$ to $R^7$ are as defined in the description and in the claims, as well as pharmaceutically acceptable salts thereof. These compounds are GPBAR1 agonists and may therefore be useful as medicaments for the treatment of diseases such as type II diabetes.

14 Claims, No Drawings

1-PYRIDAZINYL-HYDROXYIMINO-3-PHENYL-PROPANES

PRIORITY TO RELATED APPLICATION(S)

This application claims the benefit of European Patent Application No. 11188959.8, filed Nov. 14, 2011, which is hereby incorporated by reference in its entirety.

FIELD OF THE INVENTION

The present invention relates to novel 1-pyridazinyl-hydroxyimino-3-phenyl-propanes having pharmaceutical activity, their manufacture, pharmaceutical compositions containing them and their potential use as medicaments.

The compounds of the present invention are modulators or ligands of the GPBAR1 receptor. More particularly, the compounds are potent GPBAR1 agonists and may be useful for the treatment and prevention of metabolic and inflammatory diseases, in particular type II diabetes.

BACKGROUND OF THE INVENTION

Diabetes mellitus is an ever-increasing threat to human health. For example, in the United States current estimates maintain that about 16 million people suffer from diabetes mellitus. Type II diabetes also known as non-insulin-dependent diabetes mellitus accounts for approximately 90-95% of diabetes cases, killing about 230,000 U.S. residents each year. Type II diabetes is the seventh leading cause of all deaths. In Western societies, type II diabetes currently affects 6% of the adult population with world-wide frequency expected to grow by 6% per annum. Although there are certain inheritable traits that may predispose particular individuals to developing type II diabetes, the driving force behind the current increase in incidence of the disease is the increased sedentary lifestyle, diet, and obesity now prevalent in developed countries. About 80% of diabetics with type II diabetes are significantly overweight. Also, an increasing number of young people are developing the disease. Type II diabetes is now internationally recognized as one of the major threats to human health in the 21st century.

Type II diabetes manifests as inability to adequately regulate blood-glucose levels and may be characterized by a defect in insulin secretion or by insulin resistance. Namely, those who suffer from Type II diabetes have too little insulin or cannot use insulin effectively. Insulin resistance refers to the inability of the body tissues to respond properly to endogenous insulin. Insulin resistance develops because of multiple factors, including genetics, obesity, increasing age, and having high blood sugar over long periods of time. Type II diabetes, sometimes called mature on set, can develop at any age, but most commonly becomes apparent during adulthood. However, the incidence of type II diabetes in children is rising. In diabetics glucose levels build up in the blood and urine causing excessive urination, thirst, hunger, and problems with fat and protein metabolism. If left untreated, diabetes mellitus may cause life-threatening complications, including blindness, kidney failure, and heart disease.

Type II diabetes is currently treated at several levels. A first level of therapy is through diet and/or exercise, either alone or in combination with therapeutic agents. Such agents may include insulin or pharmaceuticals that lower blood glucose levels. About 49% of individuals with Type II diabetes require oral medications, about 40% require insulin injections or a combination of insulin injections and oral medications, and 10% use diet and exercise alone.

Current therapies include: insulin secretagogues, such as sulfonylureas, which increase insulin production from pancreatic β-cells; glucose-lowering effectors, such as metformin which reduce glucose production from the liver; activators of the peroxisome proliferator-activated receptor γ(PPARγ), such as the thiazolidinediones, which enhances insulin action; and α-glucosidase inhibitors which interfere with gut glucose production. There are, however, deficiencies associated with currently available treatments. For example sulfonylureas and insulin injections can be associated with hypoglycemic episodes and weight gain. Furthermore, patients often lose responsiveness to sulfonylureas over time. Metformin and α-glucosidase inhibitors often lead to gastrointestinal problems and PPARγ agonists tend to cause increased weight gain and edema.

Bile acids (BA) are amphipathic molecules which are synthesized in the liver from cholesterol and stored in the gall bladder until secretion to the duodenum and intestine to play an important role in the solubilization and absorption of dietary fat and lipid-soluble vitamins. Approx. 99% of BA are absorbed again by passive diffusion and active transport in the terminal ileum and transported back to the liver via the portal vein (enterohepatic circulation). In the liver, BA decrease their own biosynthesis from cholesterol through the activation of the farnesoid X receptor alpha (FXRα) and small heterodimer partner (SHP), leading to the transcriptional repression of cholesterol 7α-hydroxylase, the rate-limiting step of BA biosynthesis from cholesterol.

GPBAR1, in the literature termed TGR5, M-BAR or BG37 as well, was recently identified as a G-protein coupled receptor (GPCR) responsive to BA (Kawamata et al., *J. Biol. Chem.* 2003, 278, 9435-9440; Maruyama et al., *Biochem. Biophys. Res. Commun.* 2002, 298, 714-719). GPBAR1 is a G(alpha)s-coupled GPCR and stimulation by ligand binding causes activation of adenylyl cyclase which leads to the elevation of intracellular cAMP and subsequent activation of downstream signaling pathways. The human receptor shares 86, 90, 82, and 83% amino acid identity to bovine, rabbit, rat, and mouse receptor, respectively. GPBAR1 is abundantly expressed in the intestinal tract, monocytes and macrophages, lung, spleen, placenta (Kawamata et al., *J. Biol. Chem.* 2003, 278, 9435-9440). BA induced receptor internalization, intracellular cAMP production and activation of extracellular signal-regulated kinase in GPBAR1-expressing HEK293 and CHO cells.

GPBAR1 was found to be abundantly expressed in monocytes/macrophages from humans and rabbits (Kawamata et al. *J. Biol. Chem.* 2003, 278, 9435-9440), and BA treatment suppressed LPS-induced cytokine production in rabbit alveolar macrophages and human THP-1 cells expressing GPBAR1. These data suggest that bile acids can suppress the macrophage function via activation of GPBAR1. In the liver functional GPBAR1 was found in the plasma membranes of Kupffer cells, mediating inhibition of LPS-induced cytokine expression (Keitel, *Biochem. Biophys. Res. Commun.* 2008, 372, 78-84), and of sinusoidal endothelial cells, where bile salts led to an increase in intracellular cAMP and to the activation and enhanced expression of the endothelial nitric oxide (NO) synthase (Keitel, *Hepatology* 2007, 45, 695-704). Furthermore, GPBAR1 has been detected in cholangiocytes of rat liver (Keitel, *Biochem. Biophys. Res. Commun*, 2008, 372, 78-84). Hydrophobic bile acids, such as taurolithocholic acid, increase cAMP in cholangiocytes suggesting that GPBAR1 may modulate ductal secretion and bile flow. Indeed, GPBAR1 staining colocalized with the cyclic adenosine monophosphate regulated chloride channel cystic fibrosis transmembrane conductance regulator (CFTR) and the apical sodium-dependent bile salt uptake transporter (ASBT). A functional coupling of GPBAR1 to chloride secretion and bile flow has been shown using GPBAR1 agonists (Keitel et al., *Hepatology* 2009 50, 861-870; Pellicciari et al., *J Med Chem* 2009, 52(24), 7958-7961). In summary, GPBAR1 agonists may trigger a protective as well as medicative mechanism in cholestatic livers.

GPBAR1 is expressed in intestinal enteroendocrine cell lines from human (NCI-H716) and murine (STC-1, GLUTag) origin (Maruyama et al., *Biochem. Biophys. Res. Commun.* 2002, 298, 714-719). Stimulation of GPBAR1 by BA stimulated cAMP production in NCI-H716 cells. Intracellular increases in cAMP suggested that BA may induce the secretion of glucagon-like peptide-1 (GLP-1). Indeed, activation of GPBAR1 by BA promoted GLP-1 secretion in STC-1 cells (Katsuma et al., *Biochem. Biophys. Res. Commun.* 2005, 329, 386-390). Receptor-specificity has been demonstrated by RNA interference experiments which revealed that reduced expression of GPBAR1 resulted in diminished secretion of GLP-1. There is compelling evidence that GPBAR1-mediated GLP-1 and PYY release from intestinal L-cells extends to in vivo. In the isolated vascularly perfused rat colon, BAs have been shown to trigger GLP-1 secretion (Plaisancie et al., *J. Endocrin.* 1995, 145, 521-526). Using a combination of pharmacological and genetic gain- and loss-of-function studies in vivo, GPBAR1 signaling was shown to induce GLP-1 release, leading to improved liver and pancreatic function and enhanced glucose tolerance in obese mice (Thomas et al., *Cell Metabolism.* 2009, 10, 167-177). In humans, intracolonic administration of deoxycholate showed marked increases in plasma levels of GLP-1 and the co-secreted PYY (Adrian et al., *Gut* 1993, 34, 1219-1224).

GLP-1 is a peptide secreted from enteroendocrine L cells has been shown to stimulate insulin release in glucose dependent manner in humans (Kreymann et al., *Lancet* 1987, 2, 1300-1304) and studies in experimental animals demonstrated that this incretin hormone is necessary for normal glucose homeostasis. In addition, GLP-1 can exert several beneficial effects in diabetes and obesity, including 1) increased glucose disposal, 2) suppression in glucose production, 3) reduced gastric emptying, 4) reduction in food intake and 5) weight loss. More recently, much research has been focused on the use of GLP-1 in the treatment of conditions and disorders such as diabetes mellitus, stress, obesity, appetite control and satiety, Alzheimer disease, inflammation, and diseases of the central nervous system, (see, for example, Bojanowska et al., *Med. Sci. Monit.* 2005, 8, RA271-8; Perry et al., *Current Alzheimer Res.* 2005, 3, 377-385; and Meier et al., *Diabetes Metab. Res. Rev.* 2005, 2, 91-117). However, the use of a peptide in clinical treatment is limited due to difficult administration, and in vivo stability. Therefore, a small molecule that either mimics the effects of GLP-1 directly, or increases GLP-1 secretion, may be useful in treatment of the variety of conditions or disorders described above, namely diabetes mellitus.

PYY is co-secreted with GLP-1 from intestinal L-cells following a meal. A dipeptidyl peptidase-IV (DPP4) cleavage product of PYY is PYY[3-36] (Eberlein et al. *Peptides* 1989, 10, 797-803) (Grandt et al. *Regul Pept* 1994, 51, 151-159). This fragment constitutes approximately 40% of total PYY-like immunoreactivity in human and canine intestinal extracts and about 36% of total plasma PYY immunoreactivity in a fasting state to slightly over 50% following a meal. PYY[3-36] is reportedly a selective ligand at the Y2 and Y5 receptors. Peripheral administration of PYY reportedly reduces gastric acid secretion, gastric motility, exocrine pancreatic secretion (Yoshinaga et al. *Am J Physiol* 1992, 263, G695-701), gall-bladder contraction and intestinal motility (Savage et al. *Gut* 1987, 28, 166-170). It has been demonstrated that intra-arcuate (IC) or infra-peritoneal (IP) injection of PYY3-36 reduced feeding in rats and, as a chronic treatment, reduced body weight gain. Intra-venous (IV) infusion (0.8 pmol/kg/min) for 90 min of PYY3-36 reduced food intake in obese and normal human subjects 33% over 24 hours. These finding suggest that the PYY system may be a therapeutic target for the treatment of obesity (Bloom et. al. *Nature* 2002, 418, 650-654).

Furthermore, activation of GPBAR1 might be beneficial for the treatment of obesity and metabolic syndrome. Mice fed a high fat diet (HFD) containing 0.5% cholic acid gained less weight than control mice on HFD alone independent of food intake (Watanabe et al., *Nature* 2006, 439, 484-489). These effects were independent of FXR-alpha, and are likely to results from the binding of BA to GPBAR1. The proposed GPBAR1-mediated mechanism is leading to the subsequent induction of the cAMP-dependent thyroid hormone activating enzyme type 2 (D2) which converts the inactive T3 into the active T4, resulting in the stimulation of the thyroid hormone receptor and promoting energy expenditure. Mice lacking the D2 gene were resistant to cholic acid-induced weight loss. In both rodents and humans, the most thermogenically important tissues (the brown adipose and skeletal muscle) are specifically targeted by this mechanism because they co-express D2 and GPBAR1. The BA-GPBAR1-cAMP-D2 signalling pathway is therefore a crucial mechanism for fine-tuning energy homeostasis that can be targeted to improve metabolic control.

It is therefore an object of the present invention to provide selective, directly acting GPBAR1 agonists. Such agonists are useful as therapeutically active substances, particularly in the treatment and/or prevention of diseases which are associated with the activation of GPBAR1.

The novel compounds of the present invention exceed the compounds known in the art, inasmuch as they are small molecules and they bind to and selectively activate GPBAR1 very efficiently. They are expected to have an enhanced therapeutic potential compared to the compounds already known in the art and can be used for the treatment of diabetes, obesity, metabolic syndrome, hypercholesterolemia, dyslipidemia and a wide range of acute and chronic inflammatory diseases.

SUMMARY OF THE INVENTION

The present invention relates to 1-pyridazinyl-hydroxyimino-3-phenyl-propanes of the formula

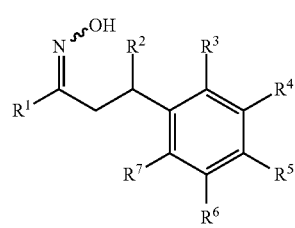

wherein
R$^1$ is heteroaryl selected from the group consisting of pyridazin-4-yl, 3-oxo-2,3-dihydro-pyridazin-4-yl and 6-oxo-1,6-dihydropyridazin-3-yl, said heteroaryl being unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy and $C_{1-7}$-alkoxy-$C_{1-7}$-alkyl;

$R^2$ is selected from the group consisting of $C_{1-7}$-alkyl, $C_{3-7}$-cycloalkyl, $C_{2-7}$-alkenyl, halogen-$C_{1-7}$-alkyl, unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl, and heteroaryl, said heteroaryl being unsubstituted or substituted by $C_{1-7}$-alkyl or oxo, $R^3$ and $R^7$ are independently from each other selected from the group consisting of hydrogen, halogen and $C_{1-7}$-alkyl; and $R^4$, $R^5$ and $R^6$ are independently selected from the group consisting of hydrogen, halogen, halogen-$C_{1-7}$-alkyl, cyano, cyano-$C_{1-7}$-alkyl, $C_{1-7}$-alkyl, $C_{3-7}$-alkenyl, $C_{1-7}$-alkynyl, $C_{1-7}$-alkoxy, $C_{1-7}$-alkoxy-$C_{1-7}$-alkyl, hydroxy, hydroxy-$C_{1-7}$-alkyl, hydroxy-$C_{3-7}$-alkenyl, hydroxy-$C_{3-7}$-alkynyl, hydroxy-$C_{1-7}$-alkoxy, carboxyl, carboxyl-$C_{1-7}$-alkyl, carboxyl-$C_{3-7}$-alkenyl, carboxyl-$C_{1-7}$-alkynyl, carboxyl-$C_{1-7}$-alkoxy, tetrazolyl, $C_{1-7}$-alkoxycarbonyl, $C_{1-7}$-alkylsulfonyl, $C_{1-7}$-alkylsulfonyloxy, $C_{1-7}$-alkylsulfonylamino, $C_{3-7}$-cycloalkylsulfonylamino, aminosulfonyl, ($C_{1-7}$-alkyl)aminosulfonyl, di-($C_{1-7}$-alkyl)-aminosulfonyl, heterocyclylsulfonyl, $C_{1-7}$-alkyl-amino, di-($C_{1-7}$-alkyl)-amino, $C_{1-7}$-alkoxy-$C_{1-7}$-alkyl-amino, $C_{1-7}$-alkoxy-$C_{1-7}$-alkyl-$C_{1-7}$-alkyl-amino, $C_{1-7}$-alkoxy-halogen-$C_{1-7}$-alkyl-amino, hydroxy-$C_{1-7}$-alkyl-$C_{1-7}$-alkyl-amino, an amino acid attached through the amino group of the amino acid, $C_{3-7}$-cycloalkyl-amino, wherein $C_{3-7}$-cycloalkyl is unsubstituted or substituted by hydroxy, hydroxy-$C_{1-7}$-alkyl or carboxyl, carboxyl-$C_{1-7}$-alkyl-aminocarbonyl, carboxyl-$C_{1-7}$-alkyl-($C_{1-7}$-alkyl)-aminocarbonyl, $C_{1-7}$-alkoxycarbonyl-$C_{1-7}$-alkyl-aminocarbonyl, $C_{1-7}$-alkyl-aminocarbonyl, di-($C_{1-7}$-alkyl)-aminocarbonyl, $C_{1-7}$-alkylsulfonyl-$C_{1-7}$-alkyl-aminocarbonyl, halogen-$C_{1-7}$-alkyl-aminocarbonyl, hydroxy-$C_{1-7}$-alkyl-aminocarbonyl, hydroxy-$C_{1-7}$-alkyl-$C_{1-7}$-alkyl-aminocarbonyl, halogen-hydroxy-$C_{1-7}$-alkyl-aminocarbonyl, $C_{1-7}$-alkoxy-$C_{1-7}$-alkyl-aminocarbonyl, $C_{3-7}$-cycloalkylaminocarbonyl, wherein $C_{3-7}$-cycloalkyl is unsubstituted or substituted by hydroxy, hydroxy-$C_{1-7}$-alkyl or carboxyl, heterocyclyl-aminocarbonyl, wherein heterocyclyl is unsubstituted or substituted by $C_{1-7}$-alkyl or oxo, heterocyclyl-$C_{1-7}$-alkyl-aminocarbonyl, wherein heterocyclyl is unsubstituted or substituted by $C_{1-7}$-alkyl or oxo, hydroxy-$C_{1-7}$-alkyl-aminocarbonyl-$C_{1-7}$-alkyl, $C_{1-7}$-alkoxycarbonyl-$C_{1-7}$-alkyl, di-($C_{1-7}$-alkoxycarbonyl)-$C_{1-7}$-alkyl, $C_{1-7}$-alkylcarbonylamino-$C_{1-7}$-alkylaminocarbonyl, $C_{1-7}$-alkylcarbonylamino, carboxyl-$C_{1-7}$-alkylcarbonylamino, $C_{1-7}$-alkoxycarbonyl-$C_{1-7}$-alkylcarbonylamino, $C_{3-7}$-cycloalkyl, wherein $C_{3-7}$-cycloalkyl is unsubstituted or substituted by hydroxy, hydroxy-$C_{1-7}$-alkyl or carboxy, $C_{3-7}$-cycloalkyl-$C_{1-7}$-alkyl, wherein $C_{3-7}$-cycloalkyl is unsubstituted or substituted by hydroxy, hydroxy-$C_{1-7}$-alkyl or carboxyl, heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl, heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl, heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl, phenyloxy, wherein phenyl is unsubstituted or substituted by one to three groups selected from halogen or carboxyl, and phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkylaminocarbonyl and carboxyl-$C_{1-7}$-alkyl-aminocarbonyl; or pharmaceutically acceptable salts thereof.

The invention is further concerned with processes for the manufacture of compounds of formula I.

The invention also relates to pharmaceutical compositions comprising a compound of formula I as described above and a pharmaceutically acceptable carrier and/or adjuvant.

A further aspect of the invention are compounds of formula I for use as therapeutic active substances, in particular for the treatment of diseases which are associated with the modulation of GPBAR1 activity. The invention thus also relates to a method for the treatment of a disease associated with the modulation of GPBAR1 activity such as for example diabetes, particularly type II diabetes or gestational diabetes.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

The nomenclature used in this application is based on IUPAC systematic nomenclature, unless indicated otherwise.

The term "compound(s) of this invention" and "compound(s) of the present invention" refers to compounds of formula I and stereoisomers, solvates or salts thereof (e.g., pharmaceutically acceptable salts).

The term "substituent" denotes an atom or a group of atoms replacing a hydrogen atom on the parent molecule.

The term "halogen" refers to fluoro, chloro, bromo and iodo, with fluoro, chloro and bromo being of particular interest. More particularly, halogen refers to fluoro and chloro.

The term "alkyl", alone or in combination with other groups, refers to a branched or straight-chain monovalent saturated aliphatic hydrocarbon radical of one to twenty carbon atoms, particularly one to sixteen carbon atoms, more particularly one to ten carbon atoms. The term "$C_{1-10}$-alkyl" refers to a branched or straight-chain monovalent saturated aliphatic hydrocarbon radical of one to ten carbon atoms, such as e.g., methyl, ethyl, n-propyl, isopropyl, n-butyl, sec-butyl, tert-butyl, pentyl, 1,1,3,3-tetramethyl-butyl and the like. More particularly, the term "alkyl" also embraces lower alkyl groups as described below.

The term "lower alkyl" or "$C_{1-7}$-alkyl", alone or in combination, signifies a straight-chain or branched-chain alkyl group with 1 to 7 carbon atoms, in particular a straight or branched-chain alkyl group with 1 to 6 carbon atoms and more particularly a straight or branched-chain alkyl group with 1 to 4 carbon atoms. Examples of straight-chain and branched $C_{1-7}$ alkyl groups are methyl, ethyl, propyl, isopropyl, butyl, isobutyl, tert-butyl, the isomeric pentyls, the isomeric hexyls and the isomeric heptyls, in particular methyl and ethyl.

The term "lower alkenyl" or "$C_{2-7}$-alkenyl" signifies a straight-chain or branched chain hydrocarbon residue comprising an olefinic bond and 2 to 7, preferably 3 to 6, particularly preferred 3 to 4 carbon atoms. Examples of alkenyl groups are ethenyl, 1-propenyl, 2-propenyl, isopropenyl, 1-butenyl, 2-butenyl, 3-butenyl and isobutenyl, in particular 2-propenyl(allyl).

The term "lower alkynyl" or "$C_{2-7}$-alkynyl" signifies a straight-chain or branched chain hydrocarbon residue comprising a triple bond and 2 to 7 carbon atoms. Examples of lower alkynyl groups are ethynyl and 1-propynyl (—C≡C—$CH_2$).

The term "cycloalkyl" or "$C_{3-7}$-cycloalkyl" denotes a saturated moncyclic hydrocarbon group containing from 3 to 7 carbon atoms, such as cyclopropyl, cyclobutyl, cyclopentyl, cyclohexyl or cycloheptyl, more particularly cyclopropyl. In addition, the term "cycloalkyl" also embraces bicyclic hydrocarbon groups containing from 3 to 10 carbon atoms. Bicyclic means consisting of two saturated carbocycles having one or more carbon atoms in common. Examples for bicyclic cycloalkyl are bicyclo[2.2.1]heptanyl or bicyclo[2.2.2]octanyl.

The term "lower cycloalkylalkyl" or "$C_{3-7}$-cycloalkyl-$C_{1-7}$-alkyl" refers to lower alkyl groups as defined above wherein at least one of the hydrogen atoms of the lower alkyl group is replaced by a cycloalkyl group. Among the lower cycloalkylalkyl groups of particular interest resides cyclopropylmethyl.

The term "lower alkoxy" or "$C_{1-7}$-alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert-butoxy, in particular methoxy.

The term "lower alkoxyalkyl" or "$C_{1-7}$-alkoxy-$C_{1-7}$-alkyl" refers to lower alkyl groups as defined above wherein at least one of the hydrogen atoms of the lower alkyl group is replaced by a lower alkoxy group. Among the lower alkoxyalkyl groups of particular interest are methoxymethyl and 2-methoxyethyl.

The term "lower alkoxyalkoxyalkyl" or "$C_{1-7}$-alkoxy-$C_{1-7}$-alkoxy-$C_{1-7}$-alkyl" refers to lower alkyl groups as defined above wherein at least one of the hydrogen atoms of the lower alkyl group is replaced by a lower alkoxy group which itself is also substituted by a further lower alkoxy group. Among the lower alkoxyalkoxyalkyl groups of particular interest is —$(CH)_2$—O—$(CH_2)_2$—O—$CH_3$.

The term hydroxy means the group —OH.

The term "lower hydroxyalkyl" or "hydroxy-$C_{1-7}$-alkyl" refers to lower alkyl groups as defined above wherein at least one of the hydrogen atoms of the lower alkyl group is replaced by a hydroxy group. Among the particular interesting lower hydroxyalkyl groups are hydroxymethyl or hydroxyethyl.

The term "lower hydroxyalkenyl" or "hydroxy-$C_{1-7}$-alkenyl" refers to lower alkenyl groups as defined above wherein at least one of the hydrogen atoms of the lower alkenyl group is replaced by a hydroxy group. Among the particular interesting lower hydroxyalkenyl groups is 3-hydroxy-propenyl.

The term "lower hydroxyalkynyl" or "hydroxy-$C_{1-7}$-alkynyl" refers to lower alkynyl groups as defined above wherein at least one of the hydrogen atoms of the lower alkynyl group is replaced by a hydroxy group. Among the particular interesting lower hydroxyalkynyl groups is 3-hydroxy-propinyl.

The term "lower halogenalkyl" or "halogen-$C_{1-7}$-alkyl" refers to lower alkyl groups as defined above wherein at least one of the hydrogen atoms of the lower alkyl group is replaced by a halogen atom, particularly fluoro or chloro, most particularly fluoro. Among the lower halogenalkyl groups of particular interest are trifluoromethyl, difluoromethyl, trifluoroethyl, 2,2-difluoroethyl, fluoromethyl and chloromethyl, with trifluoromethyl or difluoromethyl being especially interesting.

The term "lower halogenalkoxy" or "halogen-$C_{1-7}$-alkoxy" refers to lower alkoxy groups as defined above wherein at least one of the hydrogen atoms of the lower alkoxy group is replaced by a halogen atom, particularly fluoro or chloro, most particularly fluoro. Among the lower halogenalkoxy groups of particular interest are trifluoromethoxy, difluoromethoxy, fluoromethoxy and chloromethoxy, more particularly trifluoromethoxy.

The term "carboxyl" means the group —COOH.

The term "lower carboxylalkyl" or "carboxyl-$C_{1-7}$-alkyl" refers to lower alkyl groups as defined above wherein at least one of the hydrogen atoms of the lower alkyl group is replaced by a carboxyl group. Among the lower carboxylalkyl groups or particular interest are carboxylmethyl (—$CH_2$—COOH) and carboxylethyl (—$CH_2$—$CH_2$—COOH).

The term "lower carboxylalkenyl" or "carboxyl-$C_{1-7}$-alkenyl" refers to lower alkenyl groups as defined above wherein at least one of the hydrogen atoms of the lower alkenyl group is replaced by a carboxyl group. Among the particular interesting lower carboxylalkenyl groups is 3-carboxyl-propenyl (—CH=CH—$CH_2$—COOH).

The term "lower carboxylalkynyl" or "carboxyl-$C_{1-7}$-alkynyl" refers to lower alkynyl groups as defined above wherein at least one of the hydrogen atoms of the lower alkynyl group is replaced by a carboxyl group. Among the particular interesting lower carboxylalkynyl groups is 3-carboxyl-propinyl.

The term "lower carboxylalkoxy" or "carboxyl-$C_{1-7}$-alkoxy" refers to lower alkoxy groups as defined above wherein at least one of the hydrogen atoms of the lower alkoxy group is replaced by a carboxyl group. A lower carboxylalkoxy group of particular interest is carboxylmethoxy (—O—$CH_2$—COOH).

The term "lower carboxylalkylaminocarbonyl" or "carboxyl-$C_{1-7}$-alkylaminocarbonyl" refers to aminocarbonyl as defined above wherein one of the hydrogen atoms of the amino group is replaced by carboxyl-$C_{1-7}$-alkyl. Preferred lower carboxylalkylaminocarbonyl group is —CO—NH—$CH_2$—COOH.

The term "lower alkoxycarbonyl" or "$C_{1-7}$-alkoxycarbonyl" refers to the group —COOR, wherein R is lower alkyl and the term "lower alkyl" has the previously given significance. Lower alkoxycarbonyl groups of particular interest are methoxycarbonyl or ethoxycarbonyl.

The term "lower alkoxycarbonylalkyl" or "$C_{1-7}$-alkoxycarbonyl-$C_{1-7}$-alkyl" means lower alkyl groups as defined above wherein one of the hydrogen atoms of the lower alkyl group is replaced by $C_{1-7}$-alkoxycarbonyl. A particular lower alkoxycarbonylalkyl group is —$CH_2$—$COOCH_3$.

The term "di-(lower alkoxycarbonyl)-alkyl" or "di-($C_{1-7}$-alkoxycarbonyl)-$C_{1-7}$-alkyl" means lower alkyl groups as defined above wherein two of the hydrogen atoms of the lower alkyl group are replaced by $C_{1-7}$-alkoxycarbonyl. A particular di-(lower alkoxycarbonyl)-alkyl group is —CH—(COOCH$_3$)$_2$.

The term "lower alkoxycarbonylalkoxy" or "$C_{1-7}$-alkoxycarbonyl-$C_{1-7}$-alkoxy" means a lower alkoxy group as defined above wherein one of the hydrogen atoms of the lower alkoxy group is replaced by $C_{1-7}$-alkoxycarbonyl. An example for a lower alkoxycarbonylalkoxy group is —O—CH$_2$—COOCH$_3$.

The term "lower alkoxycarbonylalkylaminocarbonyl" or "$C_{1-7}$-alkoxycarbonyl-$C_{1-7}$-alkylaminocarbonyl" refers to aminocarbonyl as defined above wherein one of the hydrogen atoms of the amino group is replaced by $C_{1-7}$-alkoxycarbonyl-$C_{1-7}$-alkyl. Preferred lower alkoxycarbonylalkylaminocarbonyl group is —CO—NH—CH$_2$—COOCH$_3$.

The term "lower alkylsulfonyl" or "$C_{1-7}$-alkylsulfonyl" means the group —S(O)$_2$—R, wherein R is a lower alkyl group as defined above. A lower alkylsulfonyl group of particular interest is methylsulfonyl.

The term "lower alkylcarbonyl" or "$C_{1-7}$-alkylcarbonyl" means the group —C(O)—R, wherein R is a lower alkyl group as defined above. A lower alkylcarbonyl group of particular interest is methylcarbonyl or acetyl.

The term "$C_{1-7}$-alkylsullfonyoxy" means the group —O—S(O)$_2$—R, wherein R is a lower alkyl group as defined above.

The term "aminosulfonyl" means the group —S(O)$_2$—NH$_2$.

The term "lower alkylaminosulfonyl" or "$C_{1-7}$-alkyl-aminosulfonyl" defines the group —S(O)$_2$—NH—R, wherein R is lower alkyl and the term "lower alkyl" has the previously given meaning. An example of a lower alkylaminosulfonyl group is methylaminosulfonyl.

The term "di-lower alkylaminosulfonyl" or "di-($C_{1-7}$-alkyl)-aminosulfonyl" defines the group —S(O)$_2$—NRR', wherein R and R' are lower alkyl groups as defined above. An example of a di-lower alkylaminosulfonyl group is dimethylaminosulfonyl.

The term "heterocyclylsulfonyl" defines a group —S(O)$_2$-Het, wherein Het is a heterocyclyl group as defined herein below.

"Amino" refers to the group —NH$_2$. The term "$C_{1-7}$-alkylamino" means a group —NHR, wherein R is lower alkyl and the term "lower alkyl" has the previously given significance. The term "di-($C_{1-7}$-alkyl)-amino" means a group —NRR', wherein R and R' are lower alkyl groups as defined above.

The term "$C_{1-7}$-alkoxy-$C_{1-7}$-alkyl-$C_{1-7}$-alkylamino" refers to a group —NRR'', wherein R is a lower alkyl group as defined above and R'' is a lower alkoxyalkyl group as defined herein.

The term "$C_{1-7}$-hydroxyalkyl-$C_{1-7}$-alkylammino" refers to a group —NRR''', wherein R is a lower alkyl group as defined above and R''' is a lower hydroxyalkyl group as defined herein.

The term "$C_{1-7}$-alkoxy-halogen-$C_{1-7}$-alkyl-amino" refers to a group —NR$^x$R$^y$, wherein R$^x$ is a lower alkyl group as defined above and R$^y$ is a lower halogenalkyl group as defined herein.

The term "cycloalkyl-amino" or "$C_{3-7}$-cycloalkyl-amino" means a group —NH—R$^C$, wherein R$^C$ is a cycloalkyl group as defined above.

The term "carboxyalkyl-alkylamino" or "carboxyl-$C_{1-7}$-alkyl-$C_{1-7}$-alkyl-amino" defines the group —NR—R$^B$, wherein R is lower alkyl as defined above and R$^B$ is lower carboxylalkyl and has the previously given meaning.

The term "lower alkylsulfonylamino" or "$C_{1-7}$-alkylsulfonylamino" defines the group —NH—S(O)$_2$—R, wherein R is lower alkyl and the term "lower alkyl" has the previously given meaning.

The term "cycloalkylsulfonylamino" or "$C_{3-7}$-cycloalkylsulfonylamino" defines the group —NH—S(O)$_2$—R$^C$, wherein R$^C$ is cycloalkyl and has the previously given meaning. An example is cyclopropylsulfonylamino.

The term "lower alkylcarbonylamino" or "$C_{1-7}$-alkylcarbonylamino" defines the group —NH—CO—R, wherein R is lower alkyl and the term "lower alkyl" has the previously given meaning.

The term "lower carboxylalkylcarbonylamino" or "carboxyl-$C_{1-7}$-alkylcarbonylamino" defines the group —NH—CO—R$^B$, wherein R$^B$ is lower carboxylalkyl and has the previously given meaning.

The term "lower alkoxycarbonyl-carboylamino" or "$C_{1-7}$-alkoxycarbonyl-carbonylamino" defines the group —NH—CO—R$^E$, wherein R$^E$ is lower alkoxycarbonyl and has the previously given meaning.

The term "lower alkoxycarbonyl-alkylcarbonylamino" or "$C_{1-7}$-alkoxycarbonyl-$C_{1-7}$-alkylcarbonylamino" defines the group —NH—CO—R—R$^E$, wherein R is a lower alkyl group as defined above and at least one of the hydrogen atoms of the lower alkyl group is replaced by a lower alkoxycarbonyl group R$^E$ as defined above.

The term "lower alkoxycarbonyl-alkylcarbonylamino-alkylsulfonyl" or "$C_{1-7}$-alkoxycarbonyl-$C_{1-7}$-alkyl-carbonylamino-$C_{1-7}$-alkylsulfonyl" refers to the group —S(O)$_2$—R—NH—CO—R'—R$^E$, wherein R and R' are lower alkyl groups as defined above and at least one of the hydrogen atoms of the lower alkyl group R' is replaced by a lower alkoxycarbonyl group R$^E$ as defined above.

The term "an amino acid attached through the amino group of the amino acid" means the substituent —NR—CHR$^A$—COOH, wherein R is hydrogen or lower alkyl as defined above and R$^A$ is the side chain of an amino acid, in particular the side chain of a natural amino acid, but R$^A$ denotes also other organic substituents such as chloromethyl.

The term "aminocarbonyl" refers to the group —CO—NH$_2$.

The term "lower alkylaminocarbonyl" or "$C_{1-7}$-alkyl-aminocarbonyl" refers to a group —CONH—R, wherein R is lower alkyl as defined herein before.

The term "lower dialkylaminocarbonyl" or "di-($C_{1-7}$-alkyl)-aminocarbonyl" refers to a group —CONRR', wherein R and R' are lower alkyl groups as defined above.

The term "lower alkylsulfonyl-lower alkylaminocarbonyl" or "$C_{1-7}$-alkylsulfonyl-$C_{1-7}$-alkyl-aminocarbonyl" refers to a group —CONR—R$^S$, wherein R is lower alkyl as defined herein before and R$^S$ is a lower alkylsulfonyl group as defined above.

The term "hydroxysulonyl" means the group —S(O)$_2$—OH.

The term "lower hydroxysulfonylalkyl-aminocarbonyl" or "hydroxysulfonyl-$C_{1-7}$-alkyl-aminocarbonyl" means a group —CONH—R$^W$, wherein R$^W$ is a lower alkyl group as defined above and wherein one of the hydrogen atoms of the lower alkyl group is replaced by —S(O)$_2$—OH. An example is —CONH—CH$_2$—CH$_2$—S(O)$_2$—OH.

The term "lower aminocarbonylalkyl" or "aminocarbonyl-$C_{1-7}$-alkyl" means lower alkyl groups as defined above wherein one of the hydrogen atoms of the lower alkyl group is replaced by aminocarbonyl. A lower aminocarbonylalkyl group of particular interest is —CH$_2$—CONH$_2$.

The term "lower halogenalkyl-aminocarbonyl" or "halogen-$C_{1-7}$-alkyl-aminocarbonyl" refers to a group —CONH—R''', wherein R''' is a lower halogenalkyl group as defined above.

The term "lower hydroxyalkyl-aminocarbonyl" or "hydroxy-$C_{1-7}$-alkyl-aminocarbonyl" means a group —CONH—R''', wherein R''' is a lower hydroxyalkyl group as defined above.

The term "lower hydroxyalkyl-aminocarbonylalkyl" or "hydroxy-$C_{1-7}$-alkyl-aminocarbonyl-$C_{1-7}$-alkyl" denotes a lower alkyl group as defined above wherein one of the hydrogen atoms of the lower alkyl group is replaced by a group —CONH—R''', wherein R''' is a lower hydroxyalkyl group as defined above.

The term "lower halogenhydroxyalkyl-aminocarbonyl" or "halogen-hydroxy-$C_{1-7}$-alkyl-aminocarbonyl" means a group —CONH—$R^N$, wherein $R^N$ is a lower hydroxyalkyl group as defined above and wherein at least one of the hydrogen atoms of the lower hydroxyalkyl group is replaced by a halogen atom, particularly fluoro or chloro.

The term "(lower hydroxyalkyl)-lower alkylaminocarbonyl" or "hydroxy-$C_{1-7}$-alkyl-$C_{1-7}$-alkylaminocarbonyl" means a group —CONR—R, wherein R is a lower alkyl group as defined herein before, in particular methyl, and R''' is a lower hydroxyalkyl group as defined above.

The term "lower alkoxyalkyl-aminocarbonyl" or "($C_{1-7}$-alkoxy-$C_{1-7}$-alkyl)-aminocarbonyl" means a group —CONH—$R^Z$, wherein $R^Z$ is a lower alkoxyalkyl group as defined above.

The term "cycloalkyl-aminocarbonyl" or "$C_{3-7}$-cycloalkyl-aminocarbonyl" means a group —CONH—$R^C$, wherein $R^C$ is a cycloalkyl group as defined above.

The term "lower carboxylalkyl-aminocarbonyl" or "carboxyl-$C_{1-7}$-alkyl-aminocarbonyl" means a group —CONH—$R^D$, wherein $R^D$ is a lower carboxylalkyl group as defined above, for example —CONH—$CH_2$—COOH.

The term "lower alkoxycarbonyl-alkyl-aminocarbonyl" or "$C_{1-7}$-alkoxycarbonyl-$C_{1-7}$-alkyl-aminocarbonyl" defines the group —CO—NH—R—R—$R^E$, wherein R is a lower alkyl group as defined above and at least one of the hydrogen atoms of the lower alkyl group is replaced by a lower alkoxycarbonyl group as defined above.

The term "heterocyclyl-aminocarbonyl" means a group —CONH-Het, wherein Het is a heterocyclyl group as defined herein below.

The term "lower heterocyclylalkyl-aminocarbonyl" or "heterocyclyl-$C_{1-7}$-alkyl-aminocarbonyl" refers to a group —CONH—$R^H$, wherein $R^H$ is a lower alkyl group as defined above wherein at least one of the hydrogen atoms of the lower alkyl group is replaced by a heterocyclyl group. as defined herein below.

The term "lower alkylcarbonylamino-alkylaminocarbonyl" or "$C_{1-7}$-alkylcarbonylamino-$C_{1-7}$-alkylaminocarbonyl" refers to aminocarbonyl as defined above wherein one of the hydrogen atoms of the amino group is replaced by $C_{1-7}$-alkylcarbonylamino-$C_{1-7}$-alkyl. An example for a lower alkylcarbonylamino-alkylaminocarbonyl group is —CO—NH—$CH_2$—$CH_2$—NH—CO—$CH_3$.

The term "phenyloxy" refers to the group —O-Ph wherein Ph is phenyl.

The term "lower phenylalkyl" or "phenyl-$C_{1-7}$-alkyl" means lower alkyl groups as defined above wherein one of the hydrogen atoms of the lower alkyl group is replaced by an optionally substituted phenyl group.

The term "lower phenylalkyl-aminocarbonyl" or "(phenyl-$C_{1-7}$-alkyl)-aminocarbonyl" means a group —CONH—$R^V$, wherein $R^V$ is a lower phenylalkyl group as defined above.

The term "heterocyclyl" refers to a saturated or partly unsaturated monocyclic or bicyclic ring containing from 3 to 10 ring atoms which can comprise one, two or three atoms selected from nitrogen, oxygen and/or sulfur. Bicyclic means consisting of two cycles having two ring atoms in common, i.e. the bridge separating the two rings is either a single bond or a chain of one or two ring atoms. Examples of monocyclic heterocyclyl rings containing in particular from 3 to 7 ring atoms include azirinyl, azetidinyl, oxetanyl, piperidinyl, piperazinyl, azepinyl, diazepanyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, thiadiazolidinyl, dihydrofuryl, tetrahydrofuryl, tetrahydropyranyl, tetrahydrothiopyranyl 1,1-dioxo-hexahydro-1,6-thiopyranyl, thiomorpholinyl and 1,1-dioxo-1λ6-thiomorpholinyl. Examples of bicyclic heterocyclyl rings are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl and 3-thia-9-aza-bicyclo[3.3.1]nonyl. Examples for partly unsaturated heterocyclyl are dihydrofuryl, imidazolinyl, dihydro-oxazolyl, tetrahydro-pyridinyl, or dihydropyranyl.

The term "lower heterocyclylalkyl" or "heterocyclyl-$C_{1-7}$-alkyl" refers to lower alkyl groups as defined above wherein at least one of the hydrogen atoms of the lower alkyl group is replaced by a heterocyclyl group as defined above.

The term "heterocyclylcarbonyl" refers to the group —CO-Het wherein Het is a heterocyclyl group as defined above.

The term "heteroaryl" in general refers to an aromatic 5- or 6-membered ring which comprises one, two, three or four atoms selected from nitrogen, oxygen and/or sulfur, such as pyridyl, pyrazinyl, pyrimidinyl, 2,4-dioxo-1H-pyrimidinyl, pyridazinyl, 2-oxo-1,2-dihydropyridinyl, pyrrolyl, oxazolyl, oxadiazolyl, isoxazolyl, thiadiazolyl, tetrazolyl, pyrazolyl, imidazolyl, furanyl, thiazolyl, isothiazolyl, triazolyl, tetrazolyl, thienyl, azepinyl, diazepinyl. The term "heteroaryl" further refers to bicyclic aromatic groups comprising from 5 to 12 ring atoms, in which one or both rings cart contain one, two or three atoms selected from nitrogen, oxygen or sulfur, such as quinolinyl, isoquinolinyl, cinnolinyl, quinazolinyl, pyrazolo[1,5-a]pyridyl, imidazo[1,2-a]pyridyl, quinoxalinyl, benzofuranyl, benzothienyl, benzothiazolyl, benzotriazolyl, indolyl and indazolyl.

The term "lower heteroarylalkyl" or "heteroaryl-$C_{1-7}$-alkyl" refers to lower alkyl groups as defined above wherein at least one of the hydrogen atoms of the lower alkyl group is replaced by a heteroaryl group as defined above. A specific example of a lower heteroarylalkyl group is tetrazolyl-$C_{1-7}$-alkyl.

The term "heteroaryl-aminocarbonyl" means a group —CONH—$R^U$, wherein $R^U$ is a heteroaryl group as defined above. A specific example of a heteroaryl-aminocarbonyl group is tetrazolylaminocarbonyl.

The term "oxo" means that a C-atom of the heterocyclyl or heteroaryl ring may be substituted by =O, thus meaning that the heterocyclyl or heteroaryl ring may contain one or more carbonyl (—CO—) groups.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

Compounds of formula I can form pharmaceutically acceptable salts. The term "pharmaceutically acceptable salts" refers to those salts which retain the biological effectiveness and properties of the free bases or free acids, which are not biologically or otherwise undesirable. Pharmaceutically acceptable salts include both acid and base addition salts. The salts are for example acid addition salts of compounds of formula I with physiologically compatible mineral acids, such as hydrochloric acid, hydrobromic acid, nitric acid, carbonic acid, sulfuric acid, sulfurous acid or phosphoric acid; or with organic acids, such as methanesulfonic acid, ethanesulfonic acid, p-toluenesulfonic acid, formic acid, acetic acid, propionic acid, glycolic acid, pyruvic acid, oxylic acid, lactic acid, trifluoroacetic acid, citric acid, fumaric acid, maleic acid, malonic acid, tartaric acid, benzoic acid, cinnamic acid, mandelic acid, embonic acid, succinic acid or salicylic acid. In addition, pharmaceutically acceptable salts may be prepared from addition of an inorganic base or an organic base to the free acid. Salts derived from an inorganic base include, but are not limited to, the sodium, potassium, lithium, ammonium, calcium, magnesium, zinc, copper, manganese and aluminium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, histidine, caffeine, procaine, hydrabamine, choline, betaine, ethylendiamine, glucosamine, methylglucamine, theobromine, piperazine, N-ethylpiperidine, piperidine and polyamine resins. The compound of formula I can also be present in the form of zwitterions. Pharmaceutically acceptable salts of compounds of formula I of particular interest are the sodium salts or salts with tertiary amines.

The compounds of formula I can also be solvated, e.g., hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers". Diastereomers have two or more chiral centers and are characterized by different physical properties, e.g. melting points, boiling points, spectral properties, and reactivities. Stereoisomers that are non-superimposable mirror images are termed "enantiomers", or sometimes optical isomers. A carbon atom bonded to four non-identical substituents is termed a "chiral center".

The term "modulator" denotes a molecule that interacts with a target. The interactions include e.g. agonistic, antagonistic, or inverse agonistic activity.

The term "agonist" denotes a compound that enhances the activity of another compound or receptor site as defined e.g. in Goodman and Gilman's "The Pharmacological Basis of Therapeutics, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist, yet binds to the same receptor binding-site.

The term "half maximal effective concentration" ($EC_{50}$) denotes the plasma concentration of a particular compound required for obtaining 50% of the maximum of a particular effect in vivo.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgment of the attending medical or veterinary practitioner, and other factors.

In detail, the present invention relates to compounds of the formula

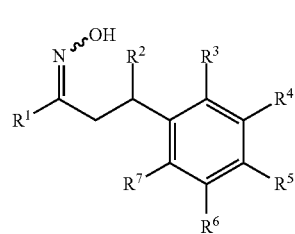

I wherein
$R^1$ is heteroaryl selected from the group consisting of pyridazin-4-yl, 3-oxo-2,3-dihydro-pyridazin-4-yl and 6-oxo-1,6-dihydropyridazin-3-yl, said heteroaryl being unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy and $C_{1-7}$-alkoxy-$C_{1-7}$-alkyl;
$R^2$ is selected from the group consisting of $C_{1-7}$-alkyl, $C_{3-7}$-cycloalkyl, $C_{2-7}$-alkenyl, halogen-$C_{1-7}$-alkyl,
unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl, and
heteroaryl, said heteroaryl being unsubstituted or substituted by $C_{1-7}$-alkyl or oxo, $R^3$ and $R^7$ are independently from each other selected from the group consisting of hydrogen, halogen and $C_{1-7}$-alkyl; and
$R^4$, $R^5$ and $R^6$ are independently selected from the group consisting of hydrogen, halogen, halogen-$C_{1-7}$-alkyl, cyano, cyano-$C_{1-7}$-alkyl,
$C_{1-7}$-alkyl, $C_{3-7}$-alkenyl, $C_{1-7}$-alkynyl,
$C_{1-7}$-alkoxy, $C_{1-7}$-alkoxy-$C_{1-7}$-alkyl,
hydroxy, hydroxy-$C_{1-7}$-alkyl, hydroxy-$C_{3-7}$-alkenyl, hydroxy-$C_{3-7}$-alkynyl, hydroxy-$C_{1-7}$-alkoxy,
carboxyl, carboxyl-$C_{1-7}$-alkyl, carboxyl-$C_{3-7}$-alkenyl, carboxyl-$C_{1-7}$-alkynyl,
carboxyl-$C_{1-7}$-alkoxy, tetrazolyl,
$C_{1-7}$-alkoxycarbonyl,
$C_{1-7}$-alkylsulfonyl, $C_{1-7}$-alkylsulfonyloxy,
$C_{1-7}$-alkylsulfonylamino, $C_{3-7}$-cycloalkylsulfonylamino,
aminosulfonyl, ($C_{1-7}$-alkyl)-aminosulfonyl, di-($C_{1-7}$-alkyl)-aminosulfonyl, heterocyclylsulfonyl,
$C_{1-7}$-alkyl-amino, di-($C_{1-7}$-alkyl)-amino, $C_{1-7}$-alkoxy-$C_{1-7}$-alkyl-amino,
$C_{1-7}$-alkoxy-$C_{1-7}$-alkyl-$C_{1-7}$-alkyl-amino, $C_{1-7}$-alkoxy-halogen-$C_{1-7}$-alkyl-amino,
hydroxy-$C_{1-7}$-alkyl-$C_{1-7}$-alkyl-amino, an amino acid attached through the amino group of the amino acid, C$_{3-7}$-cycloalkyl-amino, wherein C$_{3-7}$-cycloalkyl is unsubstituted or substituted by hydroxy, hydroxy-C$_{1-7}$-alkyl or carboxyl,
carboxyl-C$_{1-7}$-alkyl-aminocarbonyl, carboxyl-C$_{1-7}$-alkyl-(C$_{1-7}$-alkyl)-aminocarbonyl,
C$_{1-7}$-alkoxycarbonyl-C$_{1-7}$-alkyl-aminocarbonyl,
C$_{1-7}$-alkyl-aminocarbonyl, di-(C$_{1-7}$-alkyl)-aminocarbonyl,
C$_{1-7}$-alkylsulfonyl-C$_{1-7}$-alkyl-aminocarbonyl,
halogen-C$_{1-7}$-alkyl-aminocarbonyl, hydroxy-C$_{1-7}$-alkyl-aminocarbonyl,
hydroxy-C$_{1-7}$-alkyl-C$_{1-7}$-alkyl-aminocarbonyl, halogen-hydroxy-C$_{1-7}$-alkyl-aminocarbonyl,
C$_{1-7}$-alkoxy-C$_{1-7}$-alkyl-aminocarbonyl,
C$_{3-7}$-cycloalkylaminocarbonyl, wherein C$_{3-7}$-cycloalkyl is unsubstituted or substituted by hydroxy, hydroxy-C$_{1-7}$-alkyl or carboxyl,
heterocyclyl-aminocarbonyl, wherein heterocyclyl is unsubstituted or substituted by C$_{1-7}$-alkyl or oxo,
heterocyclyl-C$_{1-7}$-alkyl-aminocarbonyl, wherein heterocyclyl is unsubstituted or substituted by C$_{1-7}$-alkyl or oxo,
hydroxy-C$_{1-7}$-alkyl-aminocarbonyl-C$_{1-7}$-alkyl,
C$_{1-7}$-alkoxycarbonyl-C$_{1-7}$-alkyl,
di-(C$_{1-7}$-alkoxycarbonyl)-C$_{1-7}$-alkyl,
(C$_{1-7}$-alkylcarbonylamino-C$_{1-7}$-alkylaminocarbonyl,
C$_{1-7}$-alkylcarbonylamino, carboxyl-C$_{1-7}$-alkylcarbonylamino,
C$_{1-7}$-alkoxycarbonyl-C$_{1-7}$-alkylcarbonylamino,
C$_{3-7}$-cycloalkyl, wherein C$_{3-7}$-cycloalkyl is unsubstituted or substituted by hydroxy, hydroxy-C$_{1-7}$-alkyl or carboxyl,
C$_{3-7}$-cycloalkyl-C$_{1-7}$-alkyl, wherein C$_{3-7}$-cycloalkyl is unsubstituted or substituted by hydroxy, hydroxy-C$_{1-7}$-alkyl or carboxyl,
heterocyclyl, said heterocyclyl being unsubstituted or substituted by C$_{1-7}$-alkyl, halogen,
hydroxy, hydroxy-C$_{1-7}$-alkyl, C$_{1-7}$-alkoxy, oxo, carboxyl, carboxyl-C$_{1-7}$-alkyl, C$_{1-7}$-alkoxycarbonyl, aminocarbonyl, C$_{1-7}$-alkylsulfonyl, aminosulfonyl, C$_{1-7}$-alkylcarbonyl, carboxyl-C$_{1-7}$-alkyl-aminocarbonyl or hydroxysulfonyl-C$_{1-7}$-alkyl-aminocarbonyl,
heterocyclylcarbonyl, said heterocyclyl being unsubstituted or substituted by C$_{1-7}$-alkyl, halogen,
hydroxy, hydroxy-C$_{1-7}$-alkyl, C$_{1-7}$-alkoxy, oxo, carboxyl, carboxyl-C$_{1-7}$-alkyl or C$_{1-7}$-alkylsulfonyl,
heteroaryl, said heteroaryl being unsubstituted or substituted by C$_{1-7}$-alkyl, C$_{3-7}$-cycloalkyl,
tetrahydropyranyl, carboxyl, carboxyl-C$_{1-7}$-alkyl, C$_{1-7}$-alkoxy-C$_{1-7}$-alkyl or C$_{1-7}$-alkoxycarbonyl,
phenyloxy, wherein phenyl is unsubstituted or substituted by one to three groups selected from halogen or carboxyl, and
phenyl, said phenyl being unsubstituted or substituted by one to three groups selected from the group consisting of halogen, C$_{1-7}$-alkyl, hydroxy, hydroxy-C$_{1-7}$-alkyl, cyano, cyano-C$_{1-7}$-alkyl, amino, C$_{1-7}$-alkoxy, carboxyl, carboxyl-C$_{1-7}$-alkyl,
C$_{1-7}$-alkoxy-carbonyl, tetrazolyl, carboxyl-C$_{1-7}$-alkyl-carbonylamino,
C$_{1-7}$-alkoxy-carbonyl-C$_{1-7}$-alkyl-carbonylamino, C$_{1-7}$-alkyl-sulfonyl,
C$_{1-7}$-alkyl-sulfonylamino, aminosulfonyl, C$_{1-7}$-alkyl-aminosulfonyl,
di-(C$_{1-7}$-alkyl)-aminosulfonyl, heterocyclylsulfonyl, C$_{1-7}$-alkoxycarbonyl-C$_{1-7}$-alkoxy, C$_{1-7}$-alkoxycarbonyl-C$_{1-7}$-alkyl-aminocarbonyl, carboxyl-C$_{1-7}$-alkyl-aminocarbonyl,
C$_{1-7}$-alkoxycarbonyl-C$_{1-7}$-alkyl-carbonylamino-C$_{1-7}$-alkyl-sulfonyl,
phenyl-C$_{1-7}$-alkyl-aminocarbonyl, tetrazolyl-aminocarbonyl,
tetrazolyl-C$_{1-7}$-alkyl-aminocarbonyl and carboxyl-C$_{1-7}$-alkyl-aminocarbonyl;
or pharmaceutically acceptable salts thereof.

In one aspect, the invention relates to compounds of formula I according to the invention, wherein R$^1$ is pyridazin-4-yl, said pyridazin-4-yl being unsubstituted or substituted by one, two or three groups independently selected from the group consisting of C$_{1-7}$-alkyl, halogen, halogen-C$_{1-7}$-alkyl, hydroxy, hydroxy-C$_{1-7}$-alkyl, C$_{1-7}$-alkoxy and C$_{1-7}$-alkoxy-C$_{1-7}$-alkyl.

These are compounds of formula I having the formula

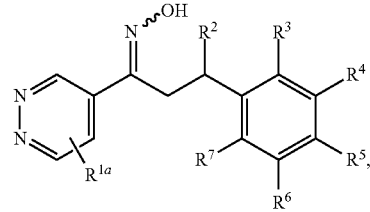

I-A wherein R$^{1a}$ is selected from the group consisting of hydrogen, C$_{1-7}$-alkyl, halogen, halogen-C$_{1-7}$-alkyl, hydroxy, hydroxy-C$_{1-7}$-alkyl, C$_{1-7}$-alkoxy and C$_{1-7}$-alkoxy-C$_{1-7}$-alkyl and R$^2$ to R$^7$ are as defined above.

More particularly, compounds of formula I are those wherein R$^1$ is pyridazin-4-yl or 3-methoxy-pyridazin-4-yl.

In another aspect, the invention relates to compounds of formula I, wherein R$^1$ is 6-oxo-1,6-dihydropyridazin-3-yl, said 6-oxo-1,6-dihydropyridazin-3-yl being unsubstituted or substituted by one, two or three groups independently selected from the group consisting of C$_{1-7}$-alkyl, halogen, halogen-C$_{1-7}$-alkyl, hydroxy, hydroxy-C$_{1-7}$-alkyl, C$_{1-7}$-alkoxy and C$_{1-7}$-alkoxy-C$_{1-7}$-alkyl.

These are compounds of formula I having the formula

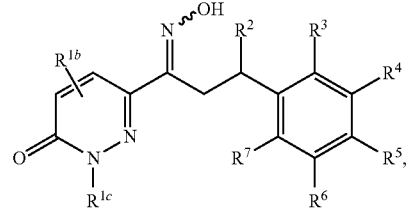

I-B wherein R$^{1b}$ is selected from the group consisting of hydrogen, C$_{1-7}$-alkyl, halogen, halogen-C$_{1-7}$-alkyl, hydroxy, hydroxy-C$_{1-7}$-alkyl, C$_{1-7}$-alkoxy and C$_{1-7}$-alkoxy-C$_{1-7}$-alkyl, R$^{1c}$ is hydrogen or C$_{1-7}$-alkyl and R$^2$ to R$^7$ are as defined above.

More particularly, the invention relates to compounds of formula I, wherein R$^1$ is 6-oxo-1,6-dihydropyridazin-3-yl or 1-methyl-6-oxo-1,6-dihydropyridazin-3-yl.

In another aspect, the invention relates to compounds of formula I, wherein R$^1$ is 3-oxo-2,3-dihydro-pyridazin-4-yl, said 3-oxo-2,3-dihydro-pyridazin-4-yl being unsubstituted or substituted by one, two or three groups independently selected from the group consisting of C$_{1-7}$-alkyl, halogen, halogen-C$_{1-7}$-alkyl, hydroxy, hydroxy-C$_{1-7}$-alkyl, C$_{1-7}$-alkoxy and C$_{1-7}$-alkoxy-C$_{1-7}$-alkyl.

These are compounds of formula I having the formula

I-C

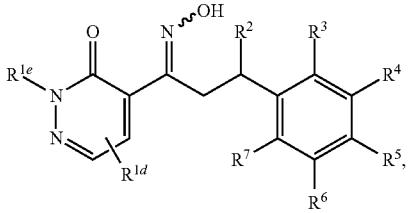

wherein $R^{1d}$ is selected from the group consisting of hydrogen, $C_{1-7}$-alkyl, halogen, halogen-$C_{1-7}$-alkyl, hydroxy, hydroxy-$C_{1-7}$-alkyl, $C_{1-7}$-alkoxy and $C_{1-7}$-alkoxy-$C_{1-7}$-alkyl, $R^{1e}$ is hydrogen or $C_{1-7}$-alkyl and $R^2$ to $R^7$ are as defined above.

More particularly, compounds of formula I of the present invention are those, wherein $R^1$ is 3-oxo-2,3-dihydro-pyridazin-4-yl or 2-methyl-3-oxo-2,3-dihydro-pyridazin-4-yl.

Thus, compounds of formula I are particularly those, wherein $R^1$ is selected from the group consisting of pyridazin-4-yl, 3-methoxy-pyridazin-4-yl, 6-oxo-1,6-dihydropyridazin-3-yl, 1-methyl-6-oxo-1,6-dihydropyridazin-3-yl, 3-oxo-2,3-dihydro-pyridazin-4-yl and 2-methyl-3-oxo-2,3-dihydro-pyridazin-4-yl.

In a further aspect, the invention relates to compounds of formula, wherein $R^2$ is unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl. In particular, the invention relates to compounds of formula I, wherein $R^2$ is 2-methylphenyl.

Furthermore, compounds of formula I according to the invention are in particular those, wherein $R^3$ and $R^7$ are hydrogen.

Compounds of formula I according to the present invention are further those, wherein $R^5$ is selected from the group consisting of
halogen, halogen-$C_{1-7}$-alkyl,
cyano, cyano-$C_{1-7}$-alkyl,
$C_{1-7}$-alkyl, $C_{3-7}$-alkenyl, $C_{1-7}$-alkynyl,
$C_{1-7}$-alkoxy, $C_{1-7}$-alkoxy-$C_{1-7}$-alkyl,
hydroxy, hydroxy-$C_{1-7}$-alkyl, hydroxy-$C_{3-7}$-alkenyl, hydroxy-$C_{3-7}$-alkynyl,
hydroxy-$C_{1-7}$-alkoxy,
carboxyl, carboxyl-$C_{1-7}$-alkyl, carboxyl-$C_{3-7}$-alkenyl, carboxyl-$C_{1-7}$-alkynyl,
carboxyl-$C_{1-7}$-alkoxy,
tetrazolyl,
$C_{1-7}$-alkoxycarbonyl,
$C_{1-7}$-alkylsulfonyl, $C_{1-7}$-alkylsulfonyloxy,
$C_{1-7}$-alkylsulfonylamino, $C_{3-7}$-cycloalkylsulfonylamino,
aminosulfonyl, ($C_{1-7}$-alkyl)-aminosulfonyl, di-($C_{1-7}$-alkyl)-aminosulfonyl, heterocyclylsulfonyl,
$C_{1-7}$-alkyl-amino, di-($C_{1-7}$-alkyl)-amino, $C_{1-7}$-alkoxy-$C_{1-7}$-alkyl-amino,
$C_{1-7}$-alkoxy-$C_{1-7}$-alkyl-$C_{1-7}$-alkyl-amino, $C_{1-7}$-alkoxy-halogen-$C_{1-7}$-alkyl-amino
hydroxy-$C_{1-7}$-alkyl-$C_{1-7}$-alkyl-amino, an amino acid attached through the amino group of the amino acid,
$C_{3-7}$-cycloalkyl-amino, wherein $C_{3-7}$-cycloalkyl is unsubstituted or substituted by hydroxy,
hydroxy-$C_{1-7}$-alkyl or carboxyl,
carboxyl-$C_{1-7}$-alkyl-aminocarbonyl, carboxyl-$C_{1-7}$-alkyl-($C_{1-7}$-alkyl)-aminocarbonyl,
$C_{1-7}$-alkoxycarbonyl-$C_1$-alkyl-aminocarbonyl,
$C_{1-7}$-alkyl-aminocarbonyl, di-($C_{1-7}$-alkyl)-aminocarbonyl,
$C_{1-7}$-alkylsulfonyl-$C_{1-7}$-alkyl-aminocarbonyl,
halogen-$C_{1-7}$-alkyl-aminocarbonyl, hydroxy-$C_{1-7}$-alkyl-aminocarbonyl,
hydroxy-$C_{1-7}$-alkyl-$C_{1-7}$-alkyl-aminocarbonyl, halogen-hydroxy-$C_{1-7}$-alkyl-aminocarbonyl,
$C_{1-7}$-alkoxy-$C_{1-7}$-alkyl-aminocarbonyl,
$C_{3-7}$-cycloalkylaminocarbonyl, wherein $C_{3-7}$-cycloalkyl is unsubstituted or substituted by hydroxy, hydroxy-$C_{1-7}$-alkyl or carboxyl,
heterocyclyl-aminocarbonyl, wherein heterocyclyl is unsubstituted or substituted by $C_{1-7}$-alkyl or oxo,
heterocyclyl-$C_{1-7}$-alkyl-aminocarbonyl, wherein heterocyclyl is unsubstituted or substituted by $C_{1-7}$-alkyl or oxo,
hydroxy-$C_{1-7}$-alkyl-aminocarbonyl-$C_{1-7}$-alkyl,
$C_{1-7}$-alkoxycarbonyl-$C_{1-7}$-alkyl,
di-($C_{1-7}$-alkoxycarbonyl)-$C_{1-7}$-alkyl,
$C_{1-7}$-alkylcarbonylamino-$C_{1-7}$-alkylaminocarbonyl,
$C_{1-7}$-alkylcarbonylamino, carboxyl-$C_{1-7}$-alkylcarbonylamino,
$C_{1-7}$-alkoxycarbonyl-$C_{1-7}$-alkylcarbonylamino,
$C_{3-7}$-cycloalkyl, wherein $C_{3-7}$-cycloalkyl is unsubstituted or substituted by hydroxy, hydroxy-$C_{1-7}$-alkyl or carboxyl,
$C_{3-7}$-cycloalkyl-$C_{1-7}$-alkyl, wherein $C_{3-7}$-cycloalkyl is unsubstituted or substituted by hydroxy, hydroxy-$C_{1-7}$-alkyl or carboxyl,
heterocyclyl, said heterocyclyl being unsubstituted or substituted by $C_{1-7}$-alkyl, halogen,
hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl,
heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl,
heteroaryl, said heteroaryl being unsubstituted or substituted by $C_{1-7}$-alkyl, $C_{3-7}$-cycloalkyl,
tetrahydropyranyl, carboxyl, carboxyl-$C_{1-7}$-alkyl, $C_{1-7}$-alkoxy-$C_{1-7}$-alkyl or $C_{1-7}$-alkoxycarbonyl, phenyloxy, wherein phenyl is unsubstituted or substituted by one to three groups selected from halogen or carboxyl, and
phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl,
amino, $C_{1-7}$-alkoxy, carboxyl, carboxyl-$C_{1-7}$-alkyl,
$C_{1-7}$-alkoxy-carbonyl, tetrazolyl, carboxyl-$C_1$-alkyl-carbonylamino,
$C_{1-7}$-alkoxy-carbonyl-$C_{1-7}$-alkyl-carbonylamino, $C_{1-7}$-alkylsulfonyl,
$C_{1-7}$-alkyl-sulfonylamino, aminosulfonyl, $C_{1-7}$-alkyl-aminosulfonyl,
di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl,
$C_{1-7}$-alkoxycarbonyl-$C_{1-7}$-alkyl-carbonylamino-$C_{1-7}$-alkyl-sulfonyl,
phenyl-$C_{1-7}$-alkyl-aminocarbonyl, tetrazolyl-aminocarbonyl,
tetrazolyl-$C_{1-7}$-alkyl-aminocarbonyl and carboxyl-$C_{1-7}$-alkyl-aminocarbonyl;
and $R^4$ and $R^6$ are hydrogen.

In particular, the invention relates to compounds of formula I, wherein $R^5$ is selected from the group consisting of halogen, halogen-$C_{1-7}$-alkyl,
cyano, cyano-$C_{17}$-alkyl, $C_{1-7}$-alkyl, $C_{3-7}$-alkenyl, $C_{1-7}$-alkynyl, $C_{1-7}$-alkoxy, $C_{1-7}$-alkoxy-$C_{1-7}$-alkyl,
hydroxy, hydroxy-$C_{1-7}$-alkyl, hydroxy-$C_{3-7}$-alkenyl, hydroxy-$C_{3-7}$-alkynyl, hydroxy-$C_{1-7}$-alkoxy,
carboxyl, carboxyl-$C_{1-7}$-alkyl, carboxyl-$C_{3-7}$-alkenyl, carboxyl-$C_{1-7}$-alkynyl, $C_{1-7}$-alkylsulfonyl,
heterocyclyl, said heterocyclyl being unsubstituted or substituted by $C_{1-7}$-alkyl, halogen,
hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl, and
phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl,
phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl;
and $R^4$ and $R^6$ are hydrogen.

More particularly, compounds of formula I according to the in, wherein $R^5$ is selected from the group consisting of halogen, halogen-$C_{1-7}$-alkyl,
carboxyl, carboxyl-$C_{1-7}$-alkyl, carboxyl-$C_{3-7}$-alkenyl, carboxyl-$C_{1-7}$-alkynyl, $C_{1-7}$-alkylsulfonyl,
heterocyclyl, said heterocyclyl being unsubstituted or substituted by carboxyl or $C_{1-7}$-alkylsulfonyl, and
phenyl, said phenyl being unsubstituted or substituted by carboxyl;
and $R^4$ and $R^6$ are hydrogen.

Even more particularly, $R^5$ is $C_{1-7}$-alkylsulfonyl or heterocyclyl, said heterocyclyl being unsubstituted or substituted by carboxyl or $C_{1-7}$-alkylsulfonyl, and $R^4$ and $R^6$ are hydrogen.

The invention also relates to compounds of formula I, wherein $R^4$, $R^5$ and $R^6$ are hydrogen.

In a further aspect, the invention relates to compounds of formula I according to the present invention, wherein $R^6$ is selected from the group consisting of
halogen, halogen-$C_{1-7}$-alkyl,
cyano, cyano-$C_{1-7}$-alkyl, $C_{1-7}$-alkyl, $C_{3-7}$-alkenyl, $C_{1-7}$-alkynyl, $C_{1-7}$-alkoxy, $C_{1-7}$-alkoxy-$C_{1-7}$-alkyl,
hydroxy, hydroxy-$C_{1-7}$-alkyl, hydroxy-$C_{3-7}$-alkenyl, hydroxy-$C_{3-7}$-alkynyl, hydroxy-$C_{1-7}$-alkoxy,
carboxyl, carboxyl-$C_{1-7}$-alkyl, carboxyl-$C_{3-7}$-alkenyl, carboxyl-$C_{1-7}$-alkynyl, carboxyl-$C_{1-7}$-alkoxy,
tetrazolyl,
$C_{1-7}$-alkoxycarbonyl, $C_{1-7}$-alkylsultonyl, $C_{1-7}$-alkylsulfonyloxy, $C_{1-7}$-alkylsulfonylamino, $C_{3-7}$-cycloalkylsulfonylamino,
aminosulfonyl, ($C_{1-7}$-alkyl)-aminosulfonyl, di-($C_{1-7}$-alkyl)-aminosulfonyl, heterocyclylsulfonyl, $C_{1-7}$-alkyl-amino, di-($C_{1-7}$-alkyl)-amino, $C_{1-7}$-alkoxy-$C_{1-7}$-alkyl-amino, $C_{1-7}$-alkoxy-$C_{1-7}$-alkyl-$C_{1-7}$-alkyl-amino, $C_{1-7}$-alkoxy-halogen-$C_{1-7}$-alkyl-amino
hydroxy-$C_{1-7}$-alkyl-$C_{1-7}$-alkyl-amino, an amino acid attached through the amino group of the amino acid,
$C_{3-7}$-cycloalkyl-amino, wherein $C_{3-7}$-cycloalkyl is unsubstituted or substituted by hydroxy, hydroxy-$C_{1-7}$-alkyl or carboxyl,
carboxyl-$C_{1-7}$-alkyl-aminocarbonyl, carboxyl-$C_{1-7}$-alkyl-($C_{1-7}$-alkyl)-aminocarbonyl, $C_{1-7}$-alkoxycarbonyl-$C_{1-7}$-alkyl-aminocarbonyl, $C_{1-7}$-alkyl-aminocarbonyl, di-($C_{1-7}$-alkyl)-aminocarbonyl, $C_{1-7}$-alkylsulfonyl-$C_{1-7}$-alkyl-aminocarbonyl,
halogen-$C_{1-7}$-alkyl-aminocarbonyl, hydroxy-$C_{1-7}$-alkyl-aminocarbonyl, hydroxy-$C_{1-7}$-alkyl-$C_{1-7}$-alkyl-aminocarbonyl, halogen-hydroxy-$C_{1-7}$-alkyl-aminocarbonyl, $C_{1-7}$-alkoxy-$C_{1-7}$-alkyl-aminocarbonyl,
$C_{3-7}$-cycloalkylaminocarbonyl, wherein $C_{3-7}$-cycloalkyl is unsubstituted or substituted by hydroxy, hydroxy-$C_{1-7}$-alkyl or carboxyl,
heterocyclyl-aminocarbonyl, wherein heterocyclyl is unsubstituted or substituted by $C_{1-7}$-alkyl or oxo,
heterocyclyl-$C_{1-7}$-alkyl-aminocarbonyl, wherein heterocyclyl is unsubstituted or substituted by $C_{1-7}$-alkyl or oxo, hydroxy-$C_{1-7}$-alkyl-aminocarbonyl-$C_{1-7}$-alkyl, $C_{1-7}$-alkoxycarbonyl-$C_{1-7}$-alkyl, di-($C_{1-7}$-alkoxycarbonyl)-$C_{1-7}$-alkyl, $C_{1-7}$-alkylcarbonylamino-$C_{1-7}$-alkylaminocarbonyl, $C_{1-7}$-alkylcarbonylamino, carboxyl-$C_{1-7}$-alkylcarbonylamino, $C_{1-7}$-alkoxycarbonyl-$C_{1-7}$-alkylcarbonylamino,
$C_{3-7}$-cycloalkyl, wherein $C_{3-7}$-cycloalkyl is unsubstituted or substituted by hydroxy, hydroxy-$C_{1-7}$-alkyl or carboxyl,
$C_{3-7}$-cycloalkyl-$C_{1-7}$-alkyl, wherein $C_{3-7}$-cycloalkyl is unsubstituted or substituted by hydroxy, hydroxy-$C_{1-7}$-alkyl or carboxyl,
heterocyclyl, said heterocyclyl being unsubstituted or substituted by $C_{1-7}$-alkyl, halogen,
hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl,
heterocyclylcarbonyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl or $C_{1-7}$-alkylsulfonyl,
heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl,
phenyloxy, wherein phenyl is unsubstituted or substituted by one to three groups selected from halogen or carboxyl, and
phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl;
and $R^4$ and $R^5$ are hydrogen.

Particular compounds of formula I are the following:
(R,E)-3-(4-bromophenyl)-1-(pyridazin-4-yl)-3-o-tolylpropan-1-one oxime, (E)-4'-(3-(hydroxyimino)-3-(pyridazin-4-yl)-1-o-tolylpropyl)biphenyl-4-carboxylic acid,
(E)-3-(4-(1-(methylsulfonyl)piperidin-4-yl)phenyl)-1-(pyridazin-4-yl)-3-o-tolylpropan-1-one oxime,
(S,E)-3-(4-bromophenyl)-1-(3-methoxypyridazin-4-yl)-3-o-tolylpropan-1-one oxime,
(S,E)-4-(3-(4-bromophenyl)-1-(hydroxyimino)-3-o-tolylpropyl)pyridazin-3(2H)-one,
(S,E)-4-(3-(4-bromophenyl)-1-(hydroxyimino)-3-o-tolylpropyl)-2-methylpyridazin-3(2H)-one,
(R,E)-6-(3-(4-bromophenyl)-1-(hydroxyimino)-3-o-tolylpropyl)-2-methylpyridazin-3 (2H)-one,
(R,E)-6-(1-(hydroxyimino)-3-(4-(1-(methylsulfonyl)piperidin-4-yl)phenyl)-3-o-tolylpropyl)-2-methylpyridazin-3(2H)-one,
(R,E)-4'-(3-(hydroxyimino)-3-(1-methyl-6-oxo-1,6-dihydropyridazin-3-yl)-1-o-tolylpropyl)biphenyl-4-carboxylic acid,
(R,E)-6-(1-(hydroxyimino)-3-(4-(methylsulfonyl)phenyl)-3-o-tolylpropyl)-2-methylpyridazin-3(2H)-one,
(R,E)-1-(3-methoxypyridazin-4-yl)-3-(4-(1-(methylsulfonyl)piperidin-4-yl)phenyl)-3-o-tolylpropan-1-one oxime,
(R,E)-4-(1-(hydroxyimino)-3-(4-(1-(methylsulfonyl)piperidin-4-yl)phenyl)-3-o-tolylpropyl)pyridazin-3(2H)-one,
(R,E)-4-(1-(hydroxyimino)-3-(4-(1-(methylsulfonyl)piperidin-4-yl)phenyl)-3-o-tolylpropyl)-2-methylpyridazin-3(2H)-one,
(S,E)-6-(3-(4-bromophenyl)-1-(hydroxyimino)-3-o-tolylpropyl)pyridazin-3(2H)-one,
or pharmaceutically acceptable salts thereof.

More particularly, the invention relates to a compounds of formula I selected from:
(R,E)-6-(1-(hydroxyimino)-3-(4-(1-(methylsulfonyl)piperidin-4-yl)phenyl)-3-o-tolylpropyl)-2-methylpyridazin-3(2H)-one,
(R,E)-6)-6-(1-(hydroxyimino)-3-(4-(methylsulfonyl)phenyl)-3-o-tolylpropyl)-2-methylpyridazin-3(2H)-one,
(R,E)-1-(3-methoxypyridazin-4-yl)-3-(4-(1-(methylsulfonyl)piperidin-4-yl)phenyl)-3-o-tolylpropan-1-one oxime,
or pharmaceutically acceptable salts thereof.

The pharmaceutically acceptable salts of the compounds of formula I also individually constitute compounds of the present invention of particular interest.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

In particular, the compounds of formula I of the present invention are oximes and thus can exist in two isomeric forms at the C=N—OH double bond, i.e. the E- (or anti) and the Z- (or syn) isomer.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a ketone of the formula II

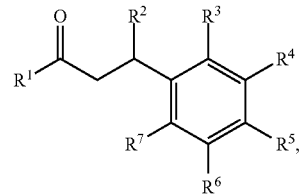

wherein $R^1$ to $R^7$ are as defined above, with hydroxylamine hydrochloride in the presence of a base to obtain a compound of the formula I

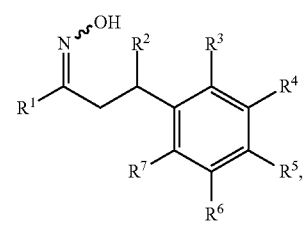

wherein $R^1$ to $R^7$ are as defined above, and, if desired, converting the compound obtained into a pharmaceutically acceptable salt.

Appropriate bases are for example are for example sodium hydroxide, sodium hydrogen carbonate or sodium acetate. The reaction is carried out in a suitable solvent such as for example ethanol, methanol, water, or mixtures thereof at temperatures between room temperature and 150° C., optionally under microwave irradiation.

Optionally, the ratio of E and Z isomers of the compound of formula I can be modified by treating the obtained compound of formula I with acids such as hydrochloric acid in solvents such as ethanol, 1,2-dimethoxyethane and dioxane or in mixtures thereof at temperatures between room temperature and reflux of the solvent. The E and Z isomers can be separated by column chromatography or by HPLC.

The invention further relates to compounds of formula I as defined above obtainable according to a process as defined above.

In detail, the compounds of formula II can be prepared as described below in schemes 1 to 5, or in analogy to the methods described below with methods known in the art. All starting materials are either conmmercially available, described in the literature or can be prepared by methods well known in the art or by methods in analogy to those described below.

Compounds of general formula II can be produced as outlined in scheme 1. $R^a$ is lower alkyl, e.g. methyl or ethyl, $R^b$ is lower alkyl, e.g. methyl, ethyl, or isopropyl.

In step a, scheme 1, ester 1 is reacted with dialkyl methyl phosphonate 2 in the presence of 2.1 equivalents of a suitable base, leading to β-ketophosphonate 3. The reaction is performed as described in the literature (J. Org. Chem. 2009, 74, 7574) in a suitable solvent, e.g., tetrahydrofuran, at temperatures around 0° C. in particular, the base is lithium diisopropylamide.

In step b, scheme 1, β-ketophosphonate 3 undergoes a Horner-Wadsworth-Emmons reaction with aldehyde 4, leading to enone 5, using conditions and reagents described in the art. Particularly, the reaction is performed in the presence of a base, e.g., potassium carbonate, triethylamine, or 1,8-diazabicycloundec-7-ene, in a solvent such as tetrahydrofuran or ethanol, at temperatures between −20° C. and the boiling point of the solvent.

In step c, scheme 1, ketone II is obtained from enone 5 by a 1,4-addition with a suitable reagent, as described in the literature. For instance, enone 5 is reacted with a Grignard reagent, $R^2$—Mg—X (X=Cl, Br, I), optionally in the presence of catalytic amounts of copper (I) iodide, in a solvent such as tetrahydrofuran, at temperatures between −78° C. and +20° C. Alternatively, in the case where $R^2$ is awryl or heteroaryl, enone 5 may be reacted with a boronic acid, $R^2B(OH)_2$, in the presence of a palladium catalyst system, e.g., palladium(II) acetate/triphenylphosphine, and a base, e.g., cesium carbonate, in toluene/chloroform, at temperatures between 60° C. and 110° C.

Scheme 1

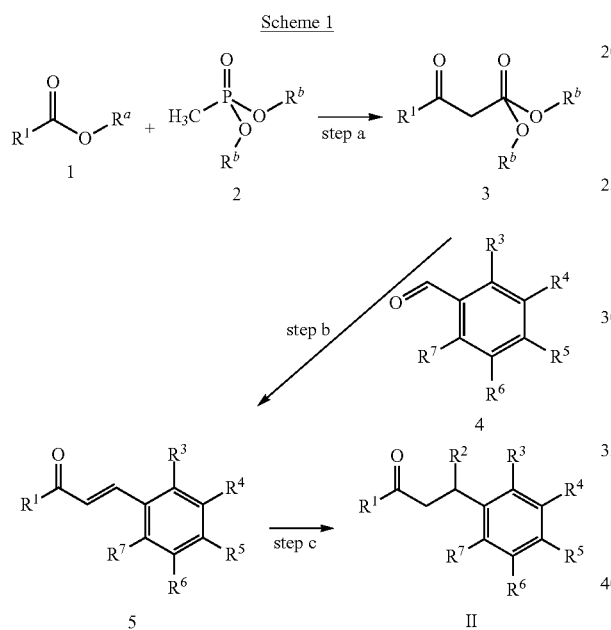

In scheme 1, $R^1$, $R^2$, $R^3$, $R^4$, $R^5$, $R^6$, and $R^7$ are as defined above.

Compounds of formula II may also be produced as outlined in scheme 2. Thus, N-methoxy-N-methylamide 6 is reacted with the anion of the pyridazine 7 at temperatures between −100° C. and 0° C., in a solvent such as toluene, tetrahydrofuran or 2-methyltetrahydrofuran. The required deprotonated pyridazine species is produced using methods described in the art, and the site of deprotonation depends on the substituent(s) $R^p$ of the pyridazine ring and on the nature of the base (*Chem. Soc. Rev.* 2008, 3, 595). For instance, in the case where $R^p$ is H, deprotonation at C(3) can be accomplished using lithium 2,2,6,6-tetramethylpiperidide in tetrahydrofuran at −75° C. (*Synthesis* 2007, 3051), whereas deprotonation at C(4) occurs using non-metallic bases such as tert-Bu-P4 base (N'''-(1,1-dimethylethyl)-N,N',N''-tris[tris(dimethylamino)phos-phoranylidene]-phosphorimidic triamide; CAS-RN [111324-04-0]) and the reaction with 6 is performed in the presence of zinc iodide (*J. Am. Chem. Soc.* 2003, 125, 8082). In the case where $R^p$ is an ortho-directing substituent such as 3-methoxy or 3-chloro, reaction of pyridazine 7 with lithium 2,2,6,6-tetramethylpiperidide leads to deprotonation at C(4).

Scheme 2

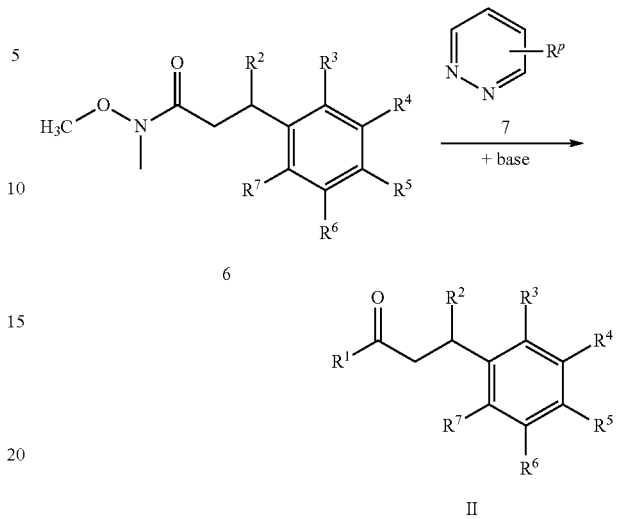

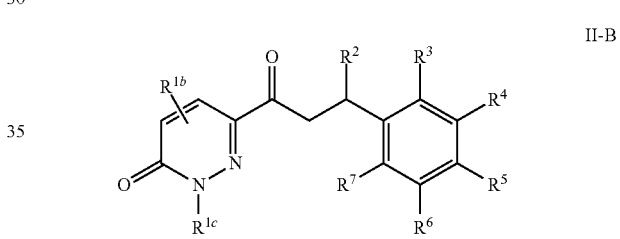

In scheme 2, $R^1$, $R^2$, $R^3$, $R^4$, $R^5$, $R^6$, and $R^7$ are as defined before.

Compounds of formula II in which $R^1$ is 6-oxo-1,6-dihydro-pyridazin-3-yl with an optional substituent $R^{1c}$ at N(1) are represented by the general formula II-B.

II-B

In formula II-B, $R^{1b}$ is selected from the group consisting of hydrogen, $C_{1-7}$-alkyl, halogen, halogen-$C_{1-7}$-alkyl, hydroxy, hydroxy-$C_{1-7}$-alkyl, $C_{1-7}$-alkoxy and $C_{1-7}$-alkoxy-$C_{1-7}$-alkyl, $R^{1c}$ is hydrogen or $C_{1-7}$-alkyl and $R^2$ to $R^7$ are as defined above.

Compounds of formula II-B can also be produced as outlined in scheme 3. In scheme 3, $R^{1c}$ is $C_{1-7}$-alkyl.

In step a, scheme 3, N-methoxy-N-methylamide 6 is reacted with the deprotonated form of 3-methoxypyridazine-1-oxide 8, leading to ketone 9. This reaction is performed at temperatures between −80° C. and −60° C., in a solvent such as tetrahydrofuran or 2-methyltetrahydrofuran and requires a base. A suitable base is lithium 2,2,6,6-tetramethylpiperidide, which selectively deprotonates 8 at C(6), at temperatures between −80° C. and −60° C.

In step b, scheme 3, the 3-methoxypyridazine-N-oxide derivative 9 is reduced to the corresponding 3-methoxypyridazine II-Aa. This deoxygenation is performed using methods and reagents known in the art, e.g., molybdenum(V) chloride in the presence of zinc dust, in a solvent such as tetrahydrofuran, at temperatures between 40° C. and 70° C. Alternatively, this reaction may be performed by way of a hydrogenation reaction using hydrogen gas at pressures between 1 bar and 100 bar in the presence of a suitable catalyst, e.g., palladium on activated charcoal, in a solvent such as ethanol or ethyl acetate, at a temperature range between 20° C. and 100° C.

Scheme 3

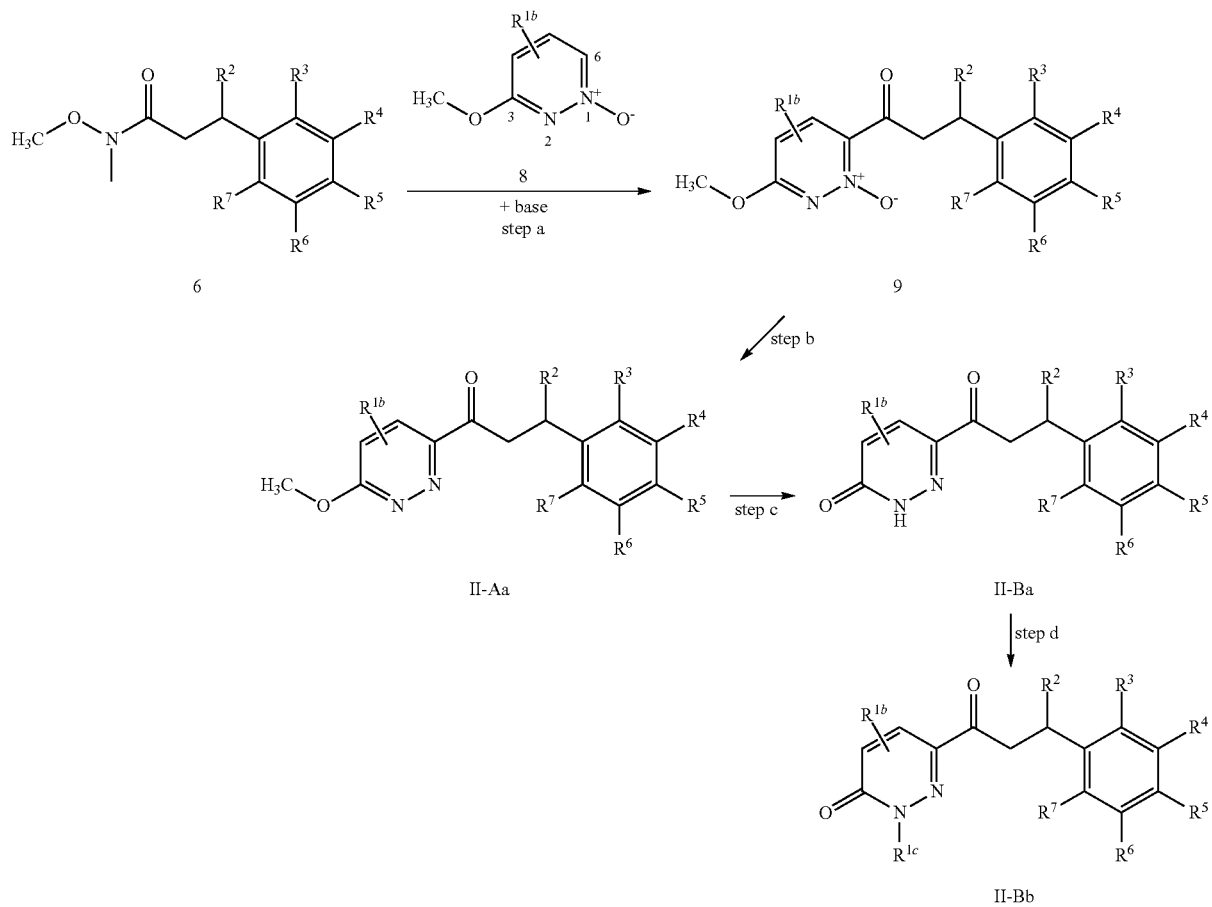

In scheme 3, $R^{1b}$, $R^2$, $R^3$, $R^4$, $R^5$, $R^6$, and $R^7$ are as defined before.

In step c, scheme 3, the methyl group of the 3-methoxypyridazine subunit of II-Aa is cleaved, leading to pyridazin-3-one II-Ba (compound of formula II-B wherein $R^{1c}$ is hydrogen. This reaction is performed in the presence of an acid, e.g. hydrochloric acid, in solvents such as water, tetrahydrofuran, 1,4-dioxane, or mixtures thereof at temperatures between 20° C. and 100° C. Alternatively, II-Ba may be produced in one step from 3-methoxypyridazine-1-oxide 9 using phosphorus tribromrnide in ethyl acetate, at temperatures between 50° C. and the boiling point of the solvent.

In optional step d, scheme 3, the N(2) of the pyridazin-3-one subunit of II-Ba is alkylated, leading to compound II-Bb. This reaction is performed using methods and reagents known in the art, e.g., using alkyl halide $R^a$—X (X=Cl, Br, I), in the presence of a base, e.g., potassium carbonate, sodium hydride, or sodium hydroxide, in a solvent such as N,N-dimethylformamide, N,N-dimethylacetamide, tetrahydrofuran, or ethanol.

N-Methoxy-N-methylamides of general formula 6 can be produced as outlined in scheme 4. $R^a$ is lower alkyl, e.g., methyl or ethyl.

Scheme 4

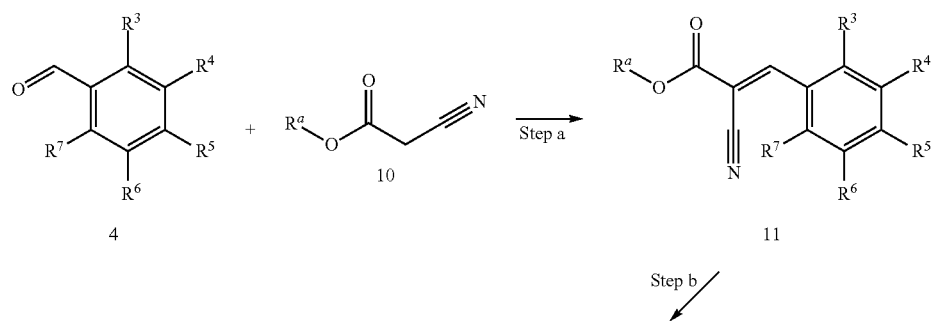

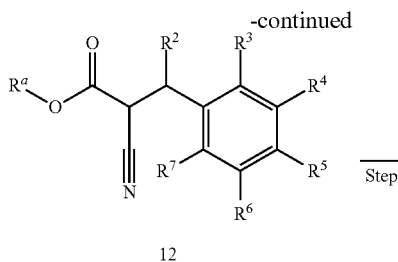
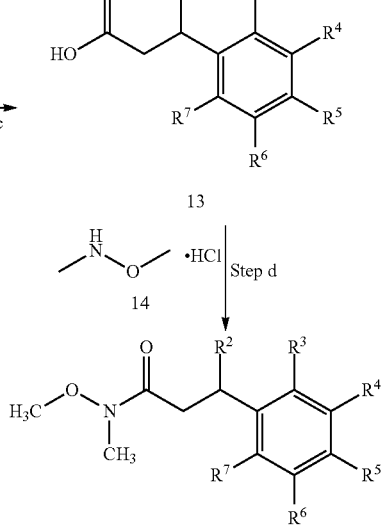

In scheme 4, $R^2$, $R^3$, $R^4$, $R^5$, $R^6$, and $R^7$ are as defined before.

In step a, scheme 4, aldehyde 4 is condensed with alkyl cyanoacetate 10, leading to 1. The reaction is performed in the presence of a base, e.g., potassium carbonate, potassium hydroxide, or piperidine, at temperatures between 20° C. and 120° C., in solvents such as ethanol, toluene, or acetic acid.

In step b, scheme 4, α,β-unsaturated cyanoester 11 undergoes a 1,4-addition reaction with an appropriate organomagnesium halide reagent, $R^2$—MgX (X=Cl, Br), leading to 12. This reaction is performed in a solvent such as toluene or tetrahydrafuran, at a temperature range between 0° C. and 110° C.

In step c, scheme 4, cyanoester 12 undergoes hydrolysis and decarboxylation, leading to carboxylic acid 13. This reaction is performed using methods and reagents known in the art, e.g. using acids such as acetic acid, sulfuric acid, hydrochloric acid or mixtures thereof, at temperatures between 60° C. and 120° C.

Carboxylic acid intermediate 13 containing an asymmetric carbon atom may be separated into its enantiomers using methods known in the art, e.g. by fractional crystallization using an optically pure chiral base, e.g., 1-phenylethylamine, or by chromatography using a chiral stationary phase.

In step d, scheme 4, carboxylic acid is converted to the N-methoxy-N-methylamide 6 using methods and reagents known in the art. For instance, the reaction is carried out using commercially available N,O-dimethylhydroxylamine hydrochloride (14) in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine, and/or 4-(dimethylamino)pyridine. Alternatively, this reaction can be performed in two steps involving first formation of the acyl halide derivative of 13 and subsequent coupling reaction with 14 in the presence of a base. Typically employed reagents for the formation of the acyl chloride are thionyl chloride, phosphorus pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, diisopropylethylamine or 4-methylmorpholine, and catalytic amounts of N,N-dimethylformamide may be used. The obtained acyl chloride can be isolated or reacted as such with 14 in an aprotic solvent, like dichloromethane, tetrahydrofuran or acetone, in the presence of a base. Typical bases are triethylamine, 4-methylmorpholine, pyridine, diisopropylethylamine or 4-(dimethylamino)pyridine or mixtures thereof.

N-Methoxy-N-methylamide derivative 6 containing an asymmetric carbon may be separated into its enantiomer using methods known in the art, e.g. chromatography using a chiral stationary phase or a chiral eluent.

Compounds of formula II in which at least one of $R^4$, $R^5$, or $R^6$ is Br are represented by the general formula II-D:

II-D

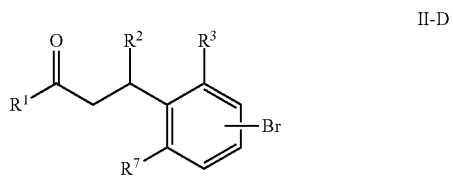

wherein $R^1$, $R^2$, $R^3$ and $R^7$ are as defined above.

Compounds of general formula II-D can further be elaborated to ketone intermediates II-E, II-F, 1-G or II-H using methods described in the literature, e.g., as outlined in scheme 5.

Scheme 5

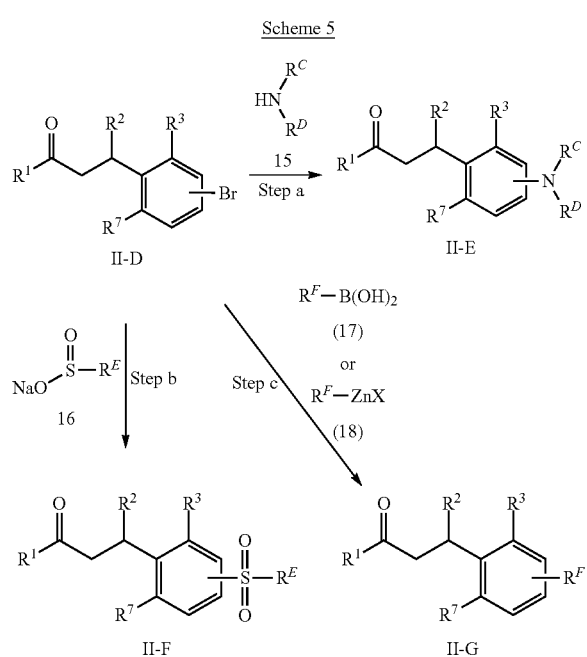

In scheme 5, $R^1$, $R^2$, $R^3$ and $R^7$ are as defined before.

For instance, for the introduction of an amine moiety Buchwald-Hartwig conditions can be used. Therefore the bromoketone II-D is reacted with a primary or secondary amine (15), leading to arylamine II-E. This reaction is performed in the presence of a catalyst system containing a palladium source such as tris(dibenzylidene-acetone)dipalladium(0) and a ligand such as 2-(di-tert-butylphosphino)biphenyl or 2-dicyclohexlphosphino-2',4',6'-triisopropylbiphenyl in the presence of a base such as sodium tert-butylate, in a solvent such as toluene or 1,4-dioxane, at temperatures between 20° C. and 110° C. (step a, scheme 5).

As shown in step b, scheme 5, bromoketone II-D can be transformed into the corresponding alkyl aryl sulfone II-F by reaction with the sodium alkanesulfinate salt 16 ($R^E$=$C_{1-7}$ alkyl). This reaction is performed using methods and reagents known in the art, e.g., in the presence of copper (I) iodide and proline sodium salt, in a solvent such as dimethyl sulfoxide, at temperatures between 100° C. and 150° C.

Suzuki reaction of bromoketone II-D with a suitably substituted boronic acid 17 ($R^F$=substituted aryl, heteroaryl, alkenyl, alkyl) or equivalent organoboron reagent leads to compound IIg (step c, scheme 5). This reaction is performed in the presence of a suitable catalyst, preferably a palladium catalyst such as dichloro[1,1'-bis(diphenylphosphino)-ferrocene]-palladium (II) dichloromethane adduct or tetrakis(triphenylphosphine)palladium (0) and a base, preferably sodium carbonate, sodium hydrogencarbonate, potassium fluoride, potassium carbonate, or triethylamine in solvents such as dioxane, water, toluene, N,N-dimethylformamide or mixtures thereof.

Similarly, compounds of formula II-D can undergo by palladium/copper co-catalyzed cross coupling with organozinc(II) halide 18 ($R^F$=substituted aryl, heteroaryl, alkenyl, alkyl, cycloalkyl, heterocyclyl; X=Cl, Br, I) as described in the art (e.g., *J. Org. Chem.* 2004, 69, 5120), thus leading to compounds II-G (step c, scheme 5). This reaction is carried out in the presence of a suitable catalyst system, e.g., [1,1'-bis(diphenylphosphino)ferrocene]-dichloropalladium(II) dichloromethane adduct and copper(I) iodide, in a solvent such as N,N-dimethylacetamide, at temperatures between 60° C. and 100° C. Organozinc(II) halides can be prepared from the corresponding halogenylalkanes as described in the experimental section.

Functional groups that are incompatible with the reaction conditions described in schemes 1-6 can be protected using methods and reagents known in the art, e.g., as described in P. J. Kocienski, "Protecting groups", (Georg Thieme Verlag, 3rd ed., 2004.

As described herein before, the compounds of formula I of the present invention can be used as medicaments for the treatment of diseases which are associated with the modulation of GPBAR1 activity.

As compounds of formula I of the invention are agonists of the GPBAR1 receptor, the compounds will be useful for lowering glucose, lipids, and insulin resistance in diabetic patients and in non-diabetic patients who have impaired glucose tolerance or who are in a pre-diabetic condition. The compounds of formula I are further useful to ameliorate hyperinsulinemia, which often occurs in diabetic or pre-diabetic patients, by modulating the swings in the level of serum glucose that often occurs in these patients. The compounds of formula I are also useful in reducing the risks associated with metabolic syndrome, in reducing the risk of developing atherosclerosis or delaying the onset of atherosclerosis, and reducing the risk of angina, claudication, heart attack, stroke, and coronary artery disease. By keeping hyperglycemia under control, the compounds are useful to delay or for preventing vascular restenosis and diabetic retinopathy.

The compounds of formula I of the present invention are useful in improving or restoring β-cell function, so that they may be useful in treating type 1 diabetes or in delaying or preventing a patient with type 2 diabetes from needing insulin therapy. The compounds may be useful for reducing appetite and body weight in obese subjects and may therefore be useful in reducing the risk of co-morbidities associated with obesity such as hypertension, atherosclerosis, diabetes, and dyslipidemia. By elevating the levels of active GLP-1 in vivo, the compounds are useful in treating neurological disorders such as Alzheimer's disease, multiple sclerosis, and schizophrenia.

Thus, the expression "diseases which are associated with the modulation of GPBAR1 activity" means diseases such as metabolic, cardiovascular, and inflammatory diseases, for example diabetes, particularly type 2 diabetes, gestational diabetes, impaired fasting glucose, impaired glucose tolerance, insulin resistance, hyperglycemia, obesity, metabolic syndrome, ischemia, myocardial infarction, retinopathy, vascular restenosis, hypercholesterolemia, hypertriglyceridemia, dyslipidemia or hyperlipidemia, lipid disorders such as low HDL cholesterol or high LDL cholesterol, high blood pressure, angina pectoris, coronary artery disease, atherosclerosis, cardiac hypertrophy, rheumatoid arthritis, asthma, chronic obstructive pulmonary disease (COPD), psoriasis, ulcerative colitis, Crohn's disease, disorders associated with parenteral nutrition especially during small bowel syndrome, irritable bowel syndrome (IBS), allergy diseases, fatty liver (e.g. non-alcoholic fatty liver disease, NAFLD), liver fibrosis (e.g. non-alcoholic steatohepatitis, NASH), primary sclerosing cholangitis (PSC), liver cirrhosis, primary biliary cirrhosis (PBC), liver colestasis, kidney fibrosis, anorexia nervosa, bulimia nervosa and neurological disorders such as Alzheimer's disease, multiple sclerosis, schizophrenia and impaired cognition.

In a particular aspect, the expression "diseases which are associated with the modulation of GPBAR1 activity" relates to diabetes, particularly type 2 diabetes, gestational diabetes, impaired fasting glucose, impaired glucose tolerance, hyperglycemia, metabolic syndrome, obesity, hypercholesterolemia and dyslipidemia.

The invention also relates to pharmaceutical compositions comprising a compound as defined above and a pharmaceutically acceptable carrier and/or adjuvant. More specifically, the invention relates to pharmaceutical compositions useful for the treatment of diseases which are associated with the modulation of GPBAR1 activity.

Further, the invention relates to compounds of formula I as defined above for use as therapeutically active substances, particularly as therapeutically active substances for the treatment of diseases which are associated with the modulation of GPBAR1 activity. In particular, the invention relates to compounds of formula I for use in diabetes, particularly type 2 diabetes, gestational diabetes, impaired fasting glucose, impaired glucose tolerance, hyperglycemia, metabolic syndrome, obesity, hypercholesterolemia and dyslipidemia, more particularly for use in diabetes, preferably type 2 diabetes, gestational diabetes or hyperglycemia.

In another aspect, the invention relates to a method for the treatment a of diseases which are associated with the modulation of GPBAR1 activity, which method comprises administering a therapeutically active amount of a compound of formula I to a human being or animal. In particular, the invention relates to a method for the treatment of diabetes, particularly type 2 diabetes, gestational diabetes, impaired fasting glucose, impaired glucose tolerance, hyperglycemia, metabolic syndrome, obesity, hypercholesterolemia and dyslipidemia, more particularly for the treatment of diabetes, preferably type 2 diabetes, gestational diabetes or hyperglycemia.

The invention further relates to the use of compounds of formula I as defined above for the treatment of diseases which are associated with the modulation of GPBAR1 activity.

In addition, the invention relates to the use of compounds of formula I as defined above for the preparation of medicaments for the treatment of diseases which are associated with the modulation of GPBAR1 activity. In particular, the invention relates to the use of compounds of formula I as defined above for the preparation of medicaments for the treatment of diabetes, particularly type 2 diabetes, gestational diabetes, impaired fasting glucose, impaired glucose tolerance, hyperglycemia, metabolic syndrome, obesity, hypercholesterolemia and dyslipidemia, more particularly for the preparation of medicaments for the treatment of diabetes, preferably type 2 diabetes, gestational diabetes or hyperglycemia.

Also contemplated herein is a combination therapy using one or more compounds of formula I or compositions of the present invention, or a pharmaceutically acceptable salts thereof in combination with one or more other pharmaceutically active compounds independently selected from the group consisting of the following:
(a) human peroxisome proliferator activated receptor (PPAR) gamma agonists (e.g., thiazolidinediones and glitazones, e.g., rosiglitazone, troglitazone, pioglitazone, englitazone, balaglitazone, and netoglitazone),
(b) biguanides such as metformin, metformin hydrochloride, buformin and phenformin,
(c) dipeptidyl peptidase IV (DPP-4) inhibitors, such as sitagliptin, sitagliptin phosphate, saxagliptin, vildagliptin, alogliptin, carmegliptin, and linagliptin,
(d) incretins such as glucagon-like peptide-1 (GLP-1) receptor agonists such as exenatide (Byetta™), liraglutide (Victoza™), GLP-1(7-36) amide and its analogs, GLP-1(7-37) and its analogs, AVE-0010 (ZP-10), R1583 (taspoglutide), GSK-716155 (albiglutide, GSK/Human Genome Sciences), BRX-0585 (Pfizer/Biorexis) and CJC-1134-PC (Exendin-4:PC-DAC™) or glucose-dependent insulinotropic peptide (GIP),
(e) insulin or insulin analogs such as LysPro insulin or inhaled formulations comprising insulin,
(f) sulfonylureas such as tolazamide, chlorpropamide, glipizide, glimepiride, glyburide, glibenclamide, tolbutamide, acetohexamide or glypizide,
(g) α-glucosidase inhibitors such as miglitol, acarbose, epalrestat, or voglibose,
(h) cholesterol biosynthesis inhibitors such as HMG CoA reductase inhibitors, e.g., lovastatin, simvastatin, pravastatin, fluvastatin, atorvastatin, rosuvastatin, cerivastatin, itavastin, nisvastatin and rivastatin, or squalene epoxidase inhibitors, e.g., terbinafine,
(i) plasma HDL-raising agents such as CETP inhibitors e.g., anacetrapib, torcetrapib and dalcetrapib, or PPAR alpha agonists, e.g., gemfibrozil, clofibrate, fenofibrate and bezafibrate,
j) PPAR dual alpha/gamma agonists such as muraglitazar, naveglitazar, aleglitazar, tesaglitazar, peliglitazar, farglitazar and JT-501,
(k) bile acid sequestrants, e.g., anion exchange resins, or quaternary amines (e.g., cholestyramine or colestipol)), or ileal bile acid transporter inhibitors (BATi);
(l) nicotinyl alcohol, nicotinic acid, niacinamide or salts thereof,
(m) cholesterol absorption inhibitors such as ezetimibe or acyl-Coenzyme A:cholesterol O-acyl transferase (ACAT) inhibitors such as avasimibe,
(n) selective estrogen receptor modulators such as raloxifene or tamoxifen) or LXR alpha or beta agonists, antagonists or partial agonists (e.g., 22(R)-hydroxycholesterol, 24(S)-hydroxycholesterol, T0901317 or GW3965);
(o) microsomal triglyceride transfer protein (MTP) inhibitors, alpha2-antagonists and imidazolines (e.g., midaglizole, isaglidole, deriglidole, idazoxan, efaroxan, fluparoxan),
(p) insulin secretagogues such as linogliride, nateglinide, repaglinide, mitiglinide calcium hydrate or meglitinide);
(q) SGLT-2 inhibitors (e.g., dapagliflozin, sergliflozin and tofoglifozin),
(s) glucokinase activators such as the compounds disclosed in e.g., WO 00/58293 A1;
(t) protein tyrosine phosphatase-1B (PIP-1B) inhibitors,
(u) glucagon receptor antagonists,
(v) anti-obesity agents such as fenfluramine, dexfenfluramine, phentiramine, sibutramine, orlistat, neuropeptide Y1 or Y5 antagonists, neuropeptide Y2 agonists, MC4R (melanocortin 4 receptor) agonists, cannabinoid receptor 1 (CB-1) antagonists/inverse agonists, and β3 adrenergic receptor agonists (e.g., GW-320659), nerve growth factor agonist (e.g., axokine), growth hormone agonists (e.g., AOD-9604), 5-HT (serotonin) reuptake/transporter inhibitors (e.g., Prozac), DA (dopamine) reuptake inhibitors (e.g., Buproprion), 5-HT, NA and DA reuptake blockers, steroidal plant extracts (e.g., P57), CCK-A (cholecystokinin-A) agonists, GHSR1a (growth hormone secretagogue receptor) antagonist/inverse agonists, ghrelin antibody, MCH1R (melanin concentrating hormone 1R) antagonists (e.g., SNAP 7941), MCH2R (melanin concentrating hormone 2R) agonist/antagonists, H3 (histamine receptor 3) inverse agonists or antagonists, H1 (histamine 1 receptor) agonists, FAS (fatty acid synthase) inhibitors, ACC-2 (acetyl-CoA carboxylase-1) inhibitors, DGAT-2 (diacylglycerol acyltransferase 2) inhibitors, DGAT-1 (diacylglycerol acyltransferase 1) inhibitors, CRF (corticotropin releasing factor) agonists, Galanin antagonists, UCP-1 (uncoupling protein-1), 2 or 3 activators, leptin or a leptin derivatives, opioid antagonists, orexin antagonists, BRS3 agonists, IL-6 agonists, a-MSH agonists, AgRP antagonists, BRS3 (bombesin receptor subtype 3) agonists, 5-HT1B agonists, POMC antagonists, CNTF (ciliary neurotrophic factor or CNTF derivative), Topiramate, glucocorticoid antagonist, 5-HT$_{2C}$ (serotonin receptor 2C) agonists (e.g., Lorcaserin), PDE (phosphodiesterase) inhibitors, fatty acid transporter inhibitors, dicarboxylate transporter inhibitors, glucose transporter inhibitors, (w) anti-inflammatory agents such as cyclooxygenase-2 (COX-2) inhibitors (e.g., rofecoxib and celecoxib); glucocorticoids, azulfidine, thrombin inhibitors (e.g., heparin, argatroban, melagatran, dabigatran) and platelet aggregation inhibitors (e.g., glycoprotein IIb/IIIa fibrinogen receptor antagonists or aspirin), and ursodeoxycholic acid (UDCA) and norursodeoxycholic acid (norUDCA) and (y) antihypertensives such as beta blockers (e.g., angiotensin II receptor antagonists such as losartan, eprosartan, irbesartan, tasosartan, telmisartan or valsartan; angiotensin converting enzyme inhibitors such as enalapril, captopril, cilazapril, ramapril, zofenopril, lisinopril and fosinopril; calcium channel blockers such as nifedipine and diltiazem and endothelian antagonists.

Such other pharmaceutically active compounds may be administered in an amount commonly used therefore, contemporaneously or sequentially with a compound of the formula I or a pharmaceutically acceptable salt thereof. In the treatment of patients who have type 2 diabetes, insulin resistance, obesity, metabolic syndrome, neurological disorders, and co-morbidities that accompany these diseases, more than one pharmaceutically active compound is commonly administered. The compounds of formula I of this invention may generally be administered to a patient who is already taking one or more other drugs for these conditions. When a compound of formula I is used contemporaneously with one or more other pharmaceutically active compounds, a pharmaceutical composition in an unit dosage form containing such other pharmaceutically active compounds and the compound of the formula I is preferred. Thus, the invention also relates to a pharmaceutical composition containing a compound of formula I in combination with one or more other pharmaceutically active compounds as defined above. When used in combination with one or more other active ingredients, the compound of formula I of the present invention and the other pharmaceutically active compounds may be used in lower doses than when each is used singly. These kinds of pharmaceutical compositions are also included in the invention.

However, the combination therapy also includes therapies in which the compound of formula I and one or more other pharmaceutically active compounds are administered in different dosage forms, but with overlapping schedules. The invention thus also relates to a method for the treatment a of diseases which are associated with the modulation of GPBAR1 activity, which method comprises administering a therapeutically active amount of a compound of formula I in combination with one or more other pharmaceutically active compounds to a human being or animal.

Pharmacological Test

The following test was carried out in order to determine the activity of the compounds of formula I:

The cDNA of the human GPBAR1 receptor (Genbank: NM_170699 with the exception of a silent C:G mutation at position 339 from the start codon) was amplified by polymerase chain reaction (PCR) from human cDNA and inserted into pCineo (Promega) by standard methods (Current Protocols in Molecular Biology, Wiley Press, ed. Ausubel et al.). The final clone was verified by DNA sequence analysis. The plasmid was transfected into CHO cells deficient in dihydrofolate reductase activity (CHO-dhfr-) using Lipofectamine plus (Invitrogen). Clones were isolated in limited dilution conditions and identified by activities in the cAMP assay using lithocholic acid as agonist. A clonal cell line displaying the greatest activity in cAMP increases was selected and identified as giving consistently good responses for up to at least 20 passages.

cAMP Assay

CHO-dhfr(minus) cells expressing human GPBAR1 receptors are seeded 17-24 hours prior to the experiment 50,000 cells per well in a black 96 well plate with flat clear bottom (Corning Costar #3904) in DMEM (Invitrogen No. 31331), 1×HT supplement, with 10% fetal calf serum and incubated at 5% $CO_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. The assay was stopped by the addition of 50 µl lysis reagent (Tris, NaCl, 1.5% Triton X100, 2.5% NP40, 10% $NaN_3$) and 50 µl detection solutions (20 µM mAb Alexa700-cAMP 1:1, and 48 µM Ruthenium-2-AHA-cAMP) and shaked for 2 h at room temperature. The time-resolved energy transfer is measured by a TRF reader (Evotec Technologies GrmbH, Hamburg Germany), equipped with a ND:YAG laser as excitation source. The plate is measured twice with the excitation at 355 nm and at the emission with a delay of 100 ns and a gate of 100 ns, total exposure time 10 s at 730 (bandwidth 30 nm) or 645 nm (bandwidth 75 nm), respectively. The measured signal at 730 nm has to be corrected for the ruthenium background, the direct excitation of Alexa and the buffer control. The FRET signal is calculated as follows: FRET=T730−Alexa730-P (T645−B645) with P=Ru730−B730/Ru645−B645, where T730 is the test well measured at 730 nM, T645 is the test well measured at 645 nm, B730 and B645 are the buffer controls at 730 nm and 645 nm, respectively, cAMP content is determined from the function of a standard curve spanning from 10 µM to 0.13 nM cAMP.

$EC_{50}$ values were determined using Activity Base analysis (ID Business Solution, Limited). The $EC_{50}$ values for a wide range of bile acids generated from this assay were in agreement with the values published in the scientific literature. Specificity for GPBAR1 was tested in non-transfected CHO cells in the same assay as above.

The compounds according to formula I have an activity in the above assay ($EC_{50}$) preferably of 0.5 nM to 10 µM, more preferably of 0.5 nM to 1 µM and most preferably of 0.5 nM to 100 nM.

For example, the following compounds showed the following human $EC_{50}$ values in the functional cAMP assay described above:

| Example | human $EC_{50}$ [µM] |
| --- | --- |
| 1 | 0.080 |
| 2 | 1.56 |
| 3 | 0.956 |
| 4 | 0.031 |
| 5 | 0.148 |
| 6 | 0.090 |
| 7 | 0.006 |
| 8 | 0.033 |
| 9 | 0.061 |
| 10 | 0.060 |

| Example | human EC$_{50}$ [μM] |
|---------|----------------------|
| 11 | 0.052 |
| 12 | 0.527 |
| 13 | 0.179 |
| 14 | 0.648 |

Pharmaceutical Compositions

The compounds of formula I and their pharmaceutically acceptable salts can be used as medicaments, e.g., in the form of pharmaceutical preparations for enteral, parenteral or topical administration. They can be administered, for example, perorally, e.g., in the form of tablets, coated tablets, dragées, hard and soft gelatin capsules, solutions, emulsions or suspensions, rectally, e.g., in the form of suppositories, parenterally, e.g., in the form of injection solutions or suspensions or infusion solutions, or topically, e.g., in the form of ointments, creams or oils. Oral administration is preferred.

The production of the pharmaceutical preparations can be effected in a manner which will be familiar to any person skilled in the art by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatin capsules. Suitable carrier materials for soft gelatin capsules are, for example, vegetable oils, waxes, fats and semi-solid and liquid polyols (depending on the nature of the active ingredient no carriers might, however, be required in the case of soft gelatin capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1-500 mg, preferably 1-100 mg, of a compound of formula I.

The following examples C1 to C5 illustrate typical compositions of the present invention, but serve merely as representative thereof.

EXAMPLE C1

Film coated tablets containing the following ingredients can be manufactured in a conventional manner:

| Ingredients | Per tablet | |
|-------------|------------|---|
| Kernel: | | |
| Compound of formula I | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

EXAMPLE C2

Capsules containing the following ingredients can be manufactured in a conventional manner:

| Ingredients | Per capsule |
|-------------|-------------|
| Compound of formula I | 25.0 mg |
| Lactose | 150.0 mg |
| Maize starch | 20.0 mg |
| Talc | 5.0 mg |

The components are sieved and mixed and filled into capsules of size 2.

EXAMPLE C3

Injection solutions can have the following composition:

| | |
|---|---|
| Compound of formula I | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE C4

Soft gelatin capsules containing the following ingredients can be manufactured in a conventional manner:

Capsule Contents

| Compound of formula I | 5.0 mg |
|---|---|
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |

Gelatin Capsule

| Gelatin | 75.0 mg |
|---|---|
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

EXAMPLE C5

Sachets containing the following ingredients can be manufactured in a conventional manner:

| Compound of formula I | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

The following examples serve to illustrate the present invention in more detail. They are, however, not intended to limit its scope in any manner.

EXAMPLES

Abbreviations

CAS RN=Chemical Abstracts registry number, EI=electron impact, HPLC=high performance liquid chromatography, min=minutes, MS=mass spectrum, sat.=saturated, aq.=aqueous, THF=tetrahydrofuran.

Example 1

(R,E)-3-(4-Bromophenyl)-1-(pyridazin-4-yl)-3-o-tolylpropan-1-one oxime

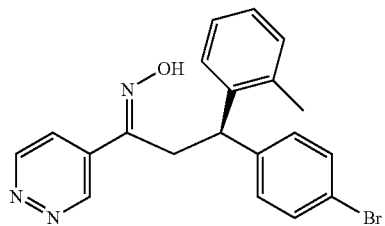 [SMILES: Cc1ccccc1[C@H](C/C(=N\O)c1ccnnc1)c1ccc(Br)cc1]

Step 1: (E)-Ethyl 3-(4-bromophenyl)-2-cyanoacrylate

To a solution of 4-bromobenzaldehyde (106 g, 573 mmol) in toluene (1000 mL) were added ethyl 2-cyanoacetate (71.3 g, 630 mmol) and piperidine (976 mg, 11.5 mmol) and the clear, light brown solution was heated at reflux for 5 h in a 4-neck flask equipped with a Dean-Stark trap, then stirred overnight at room temperature. After cooling the reaction mixture was evaporated, the residue suspended in heptane (500 mL), homogenized in an ultrasound bath for min, stirred for 20 min at 50° C., then the precipitate was collected by filtration. This was dissolved in ethyl acetate (1000 mL) and heptane (500 mL), then slowly concentrated at 50° C. to a volume of approximately 300 mL of solvent. This solution started to crystallize upon standing. The precipitate (96 g) was collected by filtration and washed with heptane/ethyl acetate 9:1 (300 mL). The mother liquor was concentrated at 50° C. until crystallization started. The product was allowed to precipitate over 1 h at room temperature, then collected by filtration to produce a second crop of product (44 g). Total yield: 140 g (87%). Light yellow solid, MS: 299.1 [M+H]$^+$.

Step 2: Ethyl 3-(4-bromophenyl)-2-cyano-3-o-tolylpropanoate

A solution of (E)-ethyl 3-(4-bromophenyl)-2-cyanoacrylate (59.4 g, 212 mmol) in toluene (420 mL) was added over 80 min at 0-5° C. to o-tolylmagnesium chloride solution (1 M in tetrahydrofuran, 276 mL, 276 mmol). The reaction mixture was heated at 85° C. for 1½ h, then poured upon ice water and partitioned between 1 M aq. hydrochloric acid solution and ethyl acetate. The organic layer was washed with brine, dried over magnesium sulfate, filtered, and evaporated to produce the title compound (84.6 g), which was directly used in the next step. Light yellow oil, MS: 370.0 [M–H]$^-$.

Step 3: 3-(4-Bromophenyl)-3-o-tolylpropanoic acid

Sulfuric acid (940 g, 9.59 mol) was added over 30 min under ice cooling to a mixture of ethyl 3-(4-bromophenyl)-2-cyano-3-o-tolylpropanoate (200 g, 494 mmol) in acetic acid (1.06 kg, 17.7 mol), while keeping the internal temperature below 27° C., then the reaction mixture was heated at reflux for 20 h. After cooling to 40° C. ice (500 g) and ethyl acetate (1500 mL) were added, the precipitate collected by filtration and washed with water to produce the title compound (34.5 g). The filtrate was partitioned between ethyl acetate and water, the organic layer was washed with brine, dried over magnesium sulfate, filtered, and evaporated. The residue was stored in the refrigerator for 1 h. Then the precipitate was collected by filtration and washed with acetic acid and heptane to afford a second crop of product (96.2 g). Total yield: 130.7 g (83%). Off-white solid, MS: 319.0 [M–H]⁻.

Step 4: 3-(4-Bromo-phenyl)-N-methoxy-N-methyl-3-o-tolyl-propionamide

To a suspension of 3-(4-bromophenyl)-3-o-tolylpropanoic acid (125.5 g, 393 mmol) in dichloromethane (600 mL) was added 1,1'-carbonyldiimidazole (79.7 g, 491 mmol) portionwise over 5 min. After gas evolution had ceased N,O-dimethylhydroxylamine hydrochloride (42.2 g, 432 mmol) was added in portions over 5 min. The reaction mixture was stirred for 17 h at room temperature, then washed with water. The organic layer was washed with brine, dried over magnesium sulfate, filtered, and evaporated. The crude product was chromatographed (SiO₂; heptane/ethyl acetate 3:1) and the product triturated with heptane to produce the title compound (127 g, 88%). White solid, MS: 362.1 [M+H]⁺.

Step 5: (R)-3-(4-Bromo-phenyl)-N-methoxy-N-methyl-3-o-tolyl-propionamide and (S)-3-(4-bromo-phenyl)-N-methoxy-N-methyl-3-o-tolyl-propionamide Separation of 3-(4-bromo-phenyl)-N-methoxy-N-methyl-3-o-tolyl-propionamide (130 g) by chiral HPLC (Reprosil Chiral-NR, heptane/2-propanol 80:20) yielded (R)-3-(4-bromo-phenyl)-N-methoxy-N-methyl-3-o-tolyl-propionamide (60 g, 46%; light yellow oil, MS: 362.1 [M+H]⁺) and (S)-3-(4-bromo-phenyl)-N-methoxy-N-methyl-3-o-tolyl-propionamide (57 g, 44%; light yellow oil, MS: 362.1 [M+H]⁺).

Step 6: (R)-3-(4-Bromophenyl)-1-(pyridazin-4-yl)-3-o-tolylpropan-1-one

To a solution of pyridazine (250 mg, 3.12 mmol) and (R)-3-(4-bromophenyl)-N-methoxy-N-methyl-3-o-tolylpropanamide (1.81 g, 4.99 mmol) in THF (10 mL) was added zinc iodide (996 mg, 3.12 mmol). The suspension was stirred for 10 min. at ambient temperature. The reaction mixture was cooled to −78° C., then N'''-(1,1-dimethylethyl)-N,N',N''-tris[tris(dimethyl-amino)phosphoranylidene]-phosphorimidic triamide solution ("Schwesinger P4 base"; 1 M in hexane 4.68 mL, 4.68 mmol) was added. The reaction mixture was allowed to reach room temperature over 16 h, then partitioned between sat, aq. ammonium chloride solution and dichloromethane. The organic layer was dried over magnesium sulfate, filtered, and evaporated. Chromatography (SiO₂; heptane-ethyl acetate gradient) produced the title compound 30 mg, 3%), while the most of the starting material was recovered (1.51 g, 83%). Light yellow gum, MS: 381.1 [M+H]⁺.

Step 7: (R,E)-3-(4-Bromophenyl)-1-(pyridazin-4-yl)-3-o-tolylpropan-1-one oxime

To a microwave vial was added (R)-3-(4-bromophenyl)-1-(pyridazin-4-yl)-3-o-tolylpropan-1-one (30 trig, 79 μmol), sodium hydrogencarbonate (20 mg, 0.24 mmol) and hydroxylamine hydrochloride (16 mg, 0.24 mmol) in ethanol (1 mL) and water (0.02 mL). The vial was capped and heated at 120° C. for 10 min, then the reaction mixture was partitioned between ethyl acetate and poured onto water. The organic layer was washed with brine, dried over magnesium sulfate, filtered, and evaporated. Chromatography (SiO₂; gradient dichloromethane to dichloromethane/methanol/25% aq. anmmonia solution 95:5:0.25) afforded the title compound (28 mg, 90%). White foam, MS: 396.1 [M+H]⁺.

Example 2

(E)-4'-(3-(hydroxyimino)-3-(pyridazin-4-yl)-1-o-tolylpropyl)biphenyl-4-carboxylic acid

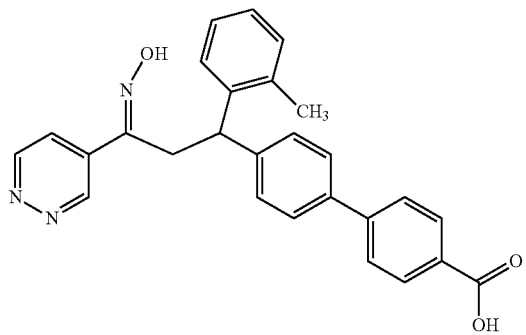 [SMILES: Cc1ccccc1C(C/C(=N\O)c1ccnnc1)c1ccc(-c2ccc(C(=O)O)cc2)cc1]

Step 1: Dimethyl 2-oxo-2-(pyridazin-4-yl)ethylphosphonate

To a solution of methylpyridazine-4-carboxylate (1.00 g, 6.95 mmol) and dimethyl methylphosphonate (889 mg, 6.95 mmol) in THF (20 ml) was added a 2 M solution of lithium diisopropylamide (2 M in THF/heptane/ethylbenzene; 7.3 ml, 14.6 mmol) between −5° C. and 0° C. Then after 5 min the reaction mixture was carefully quenched with 4 M aq. hydrochloric acid solution to adjust the pH to ca. 6 and diluted with dichloromethane. The aqueous layer was separated and extracted 2 times with dichloromethane. The combined organic layers were washed with brine, dried over magnesium sulfate, filtered, and evaporated. Chromatography (SiO₂; gradient ethyl acetate to ethyl acetate/methanol 9:1) afforded the title compound (460 mg, 29%). Dark red oil; MS: 231.1 [M+H]⁺.

Step 2: (E)-3-(4-Bromophenyl)-1-(pyridazin-4-yl)prop-2-en-1-one

To a solution of dimethyl 2-oxo-2-(pyridazin-4-yl)ethylphosphonate (1.83 g, 7.95 mmol) in THF (18 mL) was added triethylamine (885 mg, 8.75 mmol) and 4-bromobenzaldehyde (1.49 g, 7.95 mmol) at 0° C. After 6 h the reaction mixture was partitioned between water and ethyl acetate. The organic layer was washed with brine, dried over magnesium sulfate, filtered, and evaporated. The residue was suspended in ethyl acetate and the title compound (824 mg, 36%) collected by filtration. Chromatography of the mother liquor (SiO₂; ethyl acetate) produced a second crop of product (160 mg, 7%). Light yellow solid, MS: 288.9 [M+H]⁺.

Step 3: 3-(4-Bromophenyl)-1-(pyridazin-4-yl)-3-o-tolylpropan-1-one

To a suspension of copper(I) iodide (63.4 mg, 333 μmol) in tetrahydrofuran (10 ml) was added at 0° C. o-tolylmagnesium bromide solution (2 M in diethyl ether, 3.66 ml, 7.33 mmol) to give a light brown suspension. The reaction mixture was stirred at this temperature for 1½ h, then a solution of (E)-3-(4-bromophenyl)-1-(pyridazin-4-yl)prop-2-en-1-one (963 mg, 3.33 mmol) in THF (5.0 ml) was added, then after 1¾ h the reaction mixture was partitioned between sat. aq. ammonium chloride solution and ethyl acetate. The organic layer was washed with brine, dried over magnesium sulfate, filtered, and evaporated. Chromatography (SiO₂; ethyl acetate/heptane 1:1) afforded the title compound (809 mg, 64%). Light yellow foam; MS: 381.1 [M+H]⁺.

Step 4: 4'-(3-Oxo-3-(pyridazin-4-yl)-1-o-tolylpropyl)biphenyl-4-carboxylic acid

Water (1 mL) and 2 M aq. sodium carbonate solution (0.39 mL, 0.78 mmol) were added at room temperature to a degassed solution of 3-(4-bromophenyl)-1-(pyridazin-4-yl)-3-o-tolylpropan-1-one (100 mg, 262 µmol), 4-boronobenzoic acid (53.8 mg, 315 µmol) and 1,1'-bis(diphenylphosphino)ferrocene-palladium(II) dichloride dichloromethane complex (11 mg, 13 µmol) in 1,4-dioxane (1.5 mL). After heating at 80° C. for 4 h the reaction mixture was partitioned between ethyl acetate and sat. aq. ammonium chloride solution. The organic layer was washed with brine, dried over magnesium sulfate, filtered, and evaporated. After chromatography (SiO₂; gradient heptane/ethyl acetate 1:1 to ethyl acetate) the title compound was obtained (33 mg, 30%). Light yellow solid, MS: 423.2 [M+H]⁺.

Step 5: (E)-4'-(3-(Hydroxyimino)-3-(pyridazin-4-yl)-1-o-tolylpropyl)biphenyl-4-carboxylic acid The title compound was produced in analogy to example 1, step 7 from 4'-(3-oxo-3-(pyridazin-4-yl)-1-o-tolylpropyl)biphenyl-4-carboxylic acid. Light brown gum; MS: 438.2 [M+H]⁺.

Example 3

(E)-3-(4-(1-(methylsulfonyl)piperidin-4-yl)phenyl)-1-(pyridazin-4-yl)-3-o-tolylpropan-1-one oxime

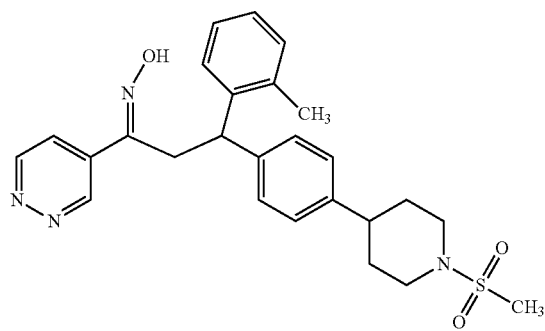 [SMILES: Cc1ccccc1C(C/C(=N\O)c1ccnnc1)c1ccc(C2CCN(S(C)(=O)=O)CC2)cc1]

Step 1: tert-butyl 4-(4-(3-oxo-3-(pyridazin-4-yl)-1-o-tolylpropyl)phenyl)piperidine-1-carboxylate To a yellow solution of 3-(4-bromophenyl)-1-(pyridazin-4-yl)-3-o-tolylpropan-1-one (example 2, step 3; 180 mg, 472 µmol) in N,N-dimethylacetamide (4 mL) were added copper(I) iodide (9 mg, 47 µmol), [1,1'-bis(diphenylphosphino)ferrocene]dichloropalladium (II) (17.3 mg, 23.6 µmol) and (1-(tert-butoxycarbonyl)piperidin-4-yl)zinc(II) iodide solution (0.5 M in N,N-dimethylacetamide, 1.9 mL, 0.95 mmol; J. Org. Chem. 2004, 69, 5120). The reaction mixture was heated at 85° C., then after 5 h another portion of copper(I) iodide (9 mg, 47 µmol), [1,1'-bis(diphenylphosphino)ferrocene]dichloropalladium(II) (17.3 mg, 23.6 µmol) was added, then after 1 h the reaction mixture was partitioned between sat. aq. ammonium chloride solution and ethyl acetate. The organic layer was washed with brine, dried over magnesium sulfate, filtered, and evaporated. The residue was suspended in ethyl acetate/heptane 1:1 and insoluble material was removed by filtration. The filtrate was purified by chromatography (SiO₂; ethyl acetate/heptane 1:1) to produce the title compound (66 mg, 29%). Orange foam, MS: 486.4 [M+H]⁺.

Step 2: 3-(4-(1-(methylsulfonyl)piperidin-4-yl)phenyl)-1-(pyridazin-4-yl)-3-o-tolylpropan-1-one To a solution of tert-butyl 4-(4-(3-oxo-3-(pyridazin-4-yl)-1-o-tolylpropyl)phenyl)-piperidine-1-carboxylate (66 mg, 136 µmol) in ethanol (1.5 mL) was added hydrogen chloride solution (4 M in 1,4-dioxane, 0.34 mL, 1.36 mmol), then after 18 h the reaction mixture was concentrated in vacuo to produce 3-(4-piperidin-4-yl-phenyl)-1-pyridazin-4-yl-3-o-tolyl-propan-1-one dihydrochloride (63 mg, light brown foam, MS: 386.4 [M+H]⁺). This was dissolved in dichloromethane (2.5 mL), then after addition of N,N-diisopropylethylamine (87.8 mg, 680 µmol) the reaction mixture was cooled to 0° C. and treated with methanesulfonyl chloride (31.1 mg, 272 µmol) was added. After 30 min the reaction mixture was partitioned between sat. aq. ammonium chloride solution and dichloromethane. The organic layer was washed with brine, dried over magnesium sulfate, filtered and evaporated. Chromatography (SiO₂; gradient dichloromethane to dichloromethane/methanol/25% aq. ammonia solution 95:5:0.25) afforded the title compound (45 mg, 71%). Light yellow foam; MS: 464.2 [M+H]⁺.

Step 4: (E)-3-(4-(1-(methylsulfonyl)piperidin-4-yl)phenyl)-1-(pyridazin-4-yl)-3-o-tolylpropan-1-one oxime The title compound was produced in analogy to example 1, step 7, from 3-(4-(1-(methylsulfonyl)piperidin-4-yl)phenyl)-1-(pyridazin-4-yl)-3-o-tolylpropan-1-one. White foam; MS: 479.2 [M+H]⁺.

Example 4

(S,E)-3-(4-bromophenyl)-1-(3-methoxypyridazin-4-yl)-3-o-tolylpropan-1-one oxime

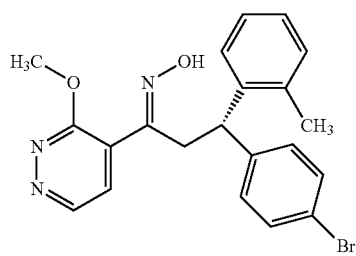 [SMILES: COc1nnccc1/C(C[C@@H](c1ccc(Br)cc1)c1ccccc1C)=N/O]

Step 1: (S)-3-(4-Bromophenyl)-1-(3-methoxypyridazin-4-yl)-3-o-tolylpropan-1-one

To a solution of 2,2,6,6-tetramethylpiperidine (1.28 g, 9.09 mmol) in THF (60 mL) was added n-butyllithium (1.6 M in hexane 6.7 mL, 9.1 mmol) at −30° C., then the solution was stirred at 0° C. for 45 min. After cooling to −70° C. a solution of 3-methoxypyridazine (1.00 g, 9.09 mmol) in THF (6 mL) was added dropwise, then a solution of (S)-3-(4-bromophenyl)-N-methoxy-N-methyl-3-o-tolylpropanamide (example 1, step 5; 823 mg, 2.27 mmol) in THF (6 mL) was added, maintaining the temperature as close as possible to −70° C. The mixture was stirred for 30 min. Sat. aq. ammonium chloride solution (30 mL) was added. The reaction mixture was allowed to reach room temperature and then extracted with ethyl acetate. The organic layer was washed with brine, dried over magnesium sulfate, filtered, and evaporated. Chromatography ($SiO_2$; heptane-ethyl acetate gradient) afforded the title compound (349 mg, 37%). Light red solid, MS: 411.1 $[M+H]^+$.

Step 2: (S,E)-3-(4-Bromophenyl)-1-(3-methoxypyridazin-4-yl)-3-o-tolylpropan-1-one oxime The title compound was produced in analogy to example 1, step 7 from (S)-3-(4-bromophenyl)-1-(3-methoxypyridazin-4-yl)-3-o-tolylpropan-1-one. White solid, MS: 426.0 $[M+H]^+$.

Example 5

(S,E)-4-(3-(4-Bromophenyl)-1-(hydroxyimino)-3-o-tolylpropyl)pyridazin-3(2H)-one

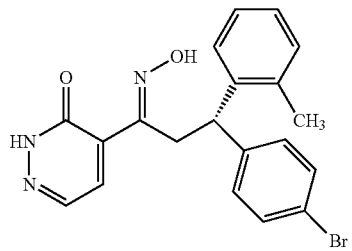 [SMILES: Cc1ccccc1[C@@H](C/C(=N\O)c1ccn[nH]c1=O)c1ccc(Br)cc1]

Step 1: (S)-4-(3-(4-Bromophenyl)-3-o-tolylpropanoyl)pyridazin-3(2H)-one

To a solution of (S)-3-(4-bromophenyl)-1-(3-methoxypyridazin-4-yl)-3-o-tolylpropan-1-one (example 4, step 1; 312 mg, 759 μmol) in 1,4-dioxane (9 ml) was added 37% aq. hydrochloric acid solution (1.27 ml, 15.2 mmol) and the resulting solution was first stirred at 60° C. for 3 h and then for 2½ h at 80° C. After cooling the reaction mixture was poured onto ice water and ethyl acetate, neutralized with sat. aq. sodium hydrogen carbonate solution and the pH was adjusted to 6.85 with 1 M aq. potassium phosphate buffer solution. The organic layer was washed with brine, dried over magnesium sulfate, filtered, and evaporated to afford the title compound (327 mg, quantitative), which was directly used in the next step. Light red foam, MS: 397.1 $[M+H]^+$.

Step 2: (S,E)-4-(3-(4-Bromophenyl)-1-(hydroxyimino)-3-o-tolylpropyl)pyridazin-3(2H)-one The title compound was produced in analogy to example 1, step 7 from (S)-4-(3-(4-bromophenyl)-3-o-tolylpropanoyl)pyridazin-3(2H)-one. White solid, MS: 412.1 $[M+H]^+$.

Example 6

(S,E)-4-(3-(4-Bromophenyl)-1-(hydroxyimino)-3-o-tolylpropyl)-2-methylpyridazin-3(2H)-one

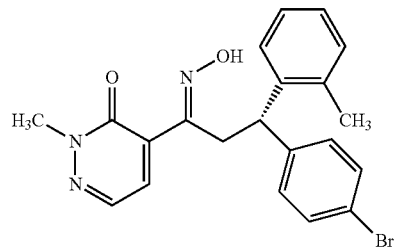 [SMILES: Cc1ccccc1[C@@H](C/C(=N\O)c1ccnn(C)c1=O)c1ccc(Br)cc1]

Step 1: (S)-4-(3-(4-Bromophenyl)-3-o-tolylpropanoyl)-2-methylpyridazin-3(2H)-one To a solution of (S)-4-(3-(4-bromophenyl)-3-o-tolylpropanoyl)pyridazin-3(2H)-one (293 mg, 679 μmol) in N,N-dimethylacetamide (4 mL) was added iodomethane (101 mg, 712 μmol) followed by potassium carbonate (103 mg, 746 μmol). The reaction mixture was stirred for 5½ h at room temperature and then partitioned between water and ethyl acetate. The organic layer was washed with brine, dried over magnesium sulfate, filtered, and evaporated. Chromatography ($SiO_2$, gradient heptane to heptane/ethyl acetate 1:1) produced the title compound (251 mg, 90%). White solid, MS: 411.2 $[M+H]^+$.

Step 2: (S,E)-4-(3-(4-Bromophenyl)-1-(hydroxyimino)-3-o-tolylpropyl)-2-methylpyridazin-3(2H)-one The title compound was produced in analogy to example 1, step 7 from (S)-4-(3-(4-bromophenyl)-3-o-tolylpropanoyl)-2-methylpyridazin-3(2H)-one. Colorless gum, MS: 426.0 $[M+H]^+$.

Example 7

(R,E)-6-(3-(4-Bromophenyl)-1-(hydroxyimino)-3-o-tolylpropyl)-2-methylpyridazin-3(2H)-one

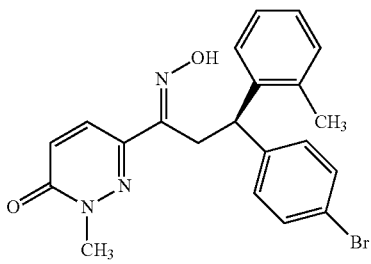 [SMILES: Cc1ccccc1[C@H](C/C(=N\O)c1ccc(=O)n(C)n1)c1ccc(Br)cc1]

Step 1: (R)-6-(3-(4-Bromophenyl)-3-o-tolylpropanoyl)-3-methoxypyridazine 1-oxide To a solution of 2,2,6,6-tetramethylpiperidine (4.21 g, 19.8 mmol) in THF (130 mL) was added n-butyllithium solution (1.6 M in hexane 12.4 mL, 19.8 mmol) at −30° C., then the solution was stirred at 0° C. for 45 min. After cooling to −70° C. a solution of 3-methoxy-pyridazine-1-oxide (*Chem.*

Pharm. Bull. 1959, 7, 938; 2.50 g, 19.8 mmol) in THF (13 mL) was added dropwise, then a solution of (R)-3-(4-bromophenyl)-N-methoxy-N-methyl-3-o-tolylpropanamide (example 1, step 5; 1.80 g, 4.95 mmol) in THF (13 mL) was added, maintaining the temperature as close as possible to −70° C. The mixture was stirred for 30 min. Then sat. aq. ammonium chloride solution (30 mL) was added. The reaction mixture was allowed to reach room temperature, then extracted with ethyl acetate. The organic layer was washed with brine, dried over magnesium sulfate, filtered, and evaporated. Chromatography (SiO$_2$; heptane-ethyl acetate gradient) afforded the title compound (2.07 g, 98%). White foam, MS: 427.0 [M+H]$^+$.

Step 2: (R)-6-(3-(4-Bromophenyl)-3-o-tolylpropanoyl)pyridazin-3(2H)-one

A mixture of (R)-6-(3-(3-(4-bromophenyl)-3-o-tolylpropanoyl)-3-methoxypyridazine 1-oxide (679 mg, 1.59 mmol) and phosphorous tribromide (2.58 g, 9.53 mmol) in ethyl acetate (15 mL) was heated at reflux for 30 min, then after cooling poured onto ice water, neutralized with sat. aq. sodium hydrogencarbonate solution and extracted with ethyl acetate. The organic layer was washed with brine, dried over magnesium sulfate, filtered, and evaporated. After chromatography (SiO$_2$; heptane-ethyl acetate gradient) the title compound was obtained (318 mg, 50%). White semisolid, MS: 397.1 [M+H]$^+$.

Step 3: (R)-6-(3-(4-Bromophenyl)-3-o-tolylpropanoyl)-2-methylpyridazin-3(2H)-one The title compound was produced in analogy to example 6, step 1 from (R)-6-(3-(4-bromophenyl)-3-o-tolylpropanoyl)pyridazin-3(2H)-one and iodomethane. White foam, MS: 411.1 [M+H]$^+$.

Step 4: (R,E)-6-(3-(4-Bromophenyl)-1-(hydroxyimino)-3-o-tolylpropyl)-2-methylpyridazin-3(2H)-one The title compound was produced in analogy to example 1, step 7 from (R)-6-(3-(4-bromophenyl)-3-o-tolylpropanoyl)-2-methylpyridazin-3(2H)-one. White solid, MS: 426.0 [M+H]$^+$.

Example 8

(R,E)-6-(1-(Hydroxyimino)-3-(4-(1-(methylsulfonyl)piperidin-4-yl)phenyl)-3-o-tolylpropyl)-2-methylpyridazin-3(2H)-one

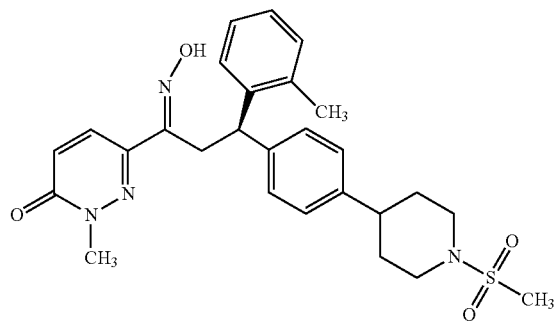 [SMILES: Cc1ccccc1[C@H](C/C(=N\O)c1ccc(=O)n(C)n1)c1ccc(C2CCN(S(C)(=O)=O)CC2)cc1]

Step 1: (R)-2-Methyl-6-(3-(4-(1-(methylsulfonyl)piperidin-4-yl)phenyl)-3-o-tolylpropanoyl)pyridazin-3(2H)-one The title compound was produced in analogy to example 3, steps 1 and 2. Thus, reaction of (R)-6-(3-(4-bromophenyl)-3-o-tolylpropanoyl)-2-methylpyridazin-3(2H)-one (example 25, step 1) with (1-(tert-butoxycarbonyl)piperidin-4-yl)zinc (II) iodide produced 4-{4-[(R)-3-(1-methyl-6-oxo-1,6-dihydro-pyridazin-3-yl)-3-oxo-1-o-tolyl-propyl]-phenyl}-piperidine-1-carboxylic acid tert-butyl ester, which after cleavage of the tert-butoxycarbonyl group led to (R)-2-methyl-6-(3-(4-(piperidin-4-yl)phenyl)-3-o-tolylpropanoyl)pyridazin-3 (2H)-one. This compound was then reacted with methanesulfonyl chloride to afford the title compound. White solid, MS: 494.3 [M+H]$^+$.

Step 2: (R,E)-6-(1-Hydroxyimino)-3-(4-(1-(methylsulfonyl)piperidin-4-yl)phenyl)-3-o-tolylpropyl)-2-methylpyridazin-3(2H)-one The title compound was produced in analogy to example 1, step 7 from (R)-2-methyl-6-(3-(4-(1-(methylsulfonyl)piperidin-4-yl)phenyl)-3-o-tolylpropanoyl)pyridazin-3(2H)-one. White solid, MS: 509.2 [M+H].

Example 9

(R,E)-4'-(3-(Hydroxyimino)-3-(1-methyl-6-oxo-1,6-dihydropyridazin-3-yl)-1-o-tolylpropyl)biphenyl-4-carboxylic acid

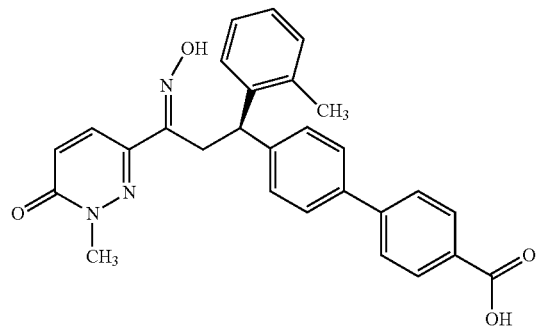 [SMILES: Cc1ccccc1[C@H](C/C(=N\O)c1ccc(=O)n(C)n1)c1ccc(-c2ccc(C(=O)O)cc2)cc1]

The title compound was produced in analogy to example 2, step 4 from (R,E)-6-(3-(4-bromophenyl)-1-(hydroxyimino)-3-o-tolylpropyl)-2-methylpyridazin-3(2H)-one (example 7). White solid, MS: 468.2 [M+H]$^+$.

Example 10

(R,E)-6-(1-(Hydroxyimino)-3-(4-(methylsulfonyl)phenyl)-3-o-tolylpropyl)-2-methylpyridazin-3(2H)-one

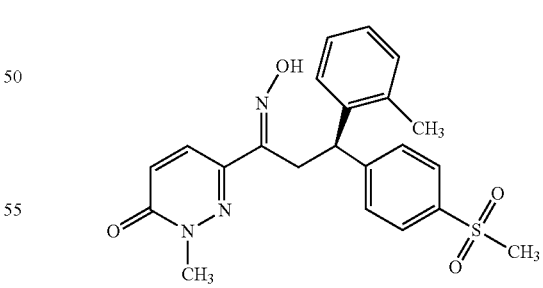

Step 1: (R)-6-(2-(2-(4-Bromophenyl)-2-o-tolylethyl)-1,3-dioxolan-2-yl)-2-methylpyridazin-3(2H)-one A solution of (R)-6-(3-(4-bromophenyl)-3-o-tolylpropanoyl)-2-methylpyridazin-3(2H)-one (example 8, step 3; 235 mg, 571 μmol), and p-toluenesulfonic acid monohydrate (10.9 mg, 57.1 μmol) in 2-ethyl-2-methyl-1,3-dioxolane (2.33 g, 20.0 mmol) was heated for 45 min at 110° C., then partitioned between sat. aq. sodium hydrogencarbonate solution and ethyl acetate. The organic layer was washed with brine, dried over magnesium sulfate, filtered, and evaporated. Chromatography (SiO$_2$; gradient heptane-ethyl acetate) produced the title compound (42 mg, 16%). White semisolid, MS: 455.1 [M+H]$^+$.

Step 2: (R)-2-Methyl-6-(2-(2-(4-methylsulfonyl)phenyl)-2-o-tolylethyl)-1,3-dioxolan-2-yl)pyridazin-3(2H)-one L-proline (7.5 mg, 65 µmol) was combined with dimethyl sulfoxide (1 ml), then sodium hydroxide (2.6 mg, 65 µmol) was added and the reaction stirred at room temperature for 30 min, then (R)-6-(2-(2-(4-bromophenyl)-2-o-tolylethyl)-1,3-dioxolan-2-yl)-2-methylpyridazin-3(2H)-one (37 mg, 81 µmol), sodium methanesulfinate (68 mg, 650 µmol) and copper(I) iodide (12.4 mg, 65 µmol) were added. The reaction mixture was heated at 120° C. for 22 h, then partitioned between water and ethyl acetate. The organic layer was washed with brine, dried over magnesium sulfate, filtered, and evaporated. Chromatography (SiO$_2$; gradient heptane-ethyl acetate) produced the title compound (10 mg, 27%). White semisolid, MS: 455.2 [M+H]$^+$.

Step 3: (R)-2-Methyl-6-(3-(4-(methylsulfonyl)phenyl)-3-o-tolylpropanoyl)pyridazin-3(2H)-one To a solution of (R)-2-methyl-6-(2-(2-(4-(methylsulfonyl)phenyl)-2-o-tolylethyl)-1,3-dioxolan-2-yl)pyridazin-3(2H)-one (10 mg, 22 µmol) in acetone (1 ml) was added bis(acetonitrile)dichloropalladium(II) (1.4 mg, 5 µmol, Eq: 0.25), then after 24 h at room temperature another portion of bis(acetonitrile)dichloropalladium(II) (6 mg, 22 µmol) was added, then after 24 h the reaction mixture was evaporated. Chromatography (SiO$_2$; gradient heptane/ethyl acetate 2:1 to ethyl acetate) afforded the title compound (5 mg, 55%). White solid, MS: 411.2 [M+H]$^+$.

Step 4: (R,E)-6-(1-(Hydroxyimino)-3-(4-(methylsulfonyl)phenyl)-3-o-tolylpropyl)-2-methylpyridazin-3(2H)-one The title compound was produced in analogy to example 1, step 7 from (R)-2-methyl-6-(3-(4-(methylsulfonyl)phenyl)-3-o-tolylpropanoyl)pyridazin-3(2H)-one. Colorless gum, MS: 426.0 [M+H]$^+$.

Example 11

(R,E)-1-(3-Methoxypyridazin-4-yl)-3-(4-(1-(methylsulfonyl)piperidin-4-yl)phenyl)-3-o-tolylpropan-1-one oxime

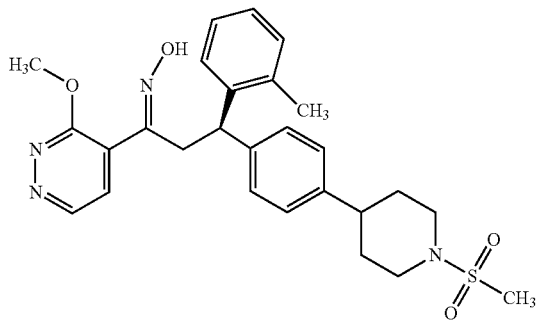 [SMILES: COc1nnccc1/C(C[C@H](c1ccc(C2CCN(S(C)(=O)=O)CC2)cc1)c1ccccc1C)=N/O]

Step 1: (R)-tert-Butyl 4-(4-(3-(methoxy(methyl)amino)-3-oxo-1-o-tolylpropyl)phenyl)-piperidine-1-carboxylate The title compound was produced in analogy to example 3, step 1 from (R)-3-(4-bromophenyl)-N-methoxy-N-methyl-3-o-tolylpropanamide (examples 1 and 2, step 5) and (1-(tert-butoxycarbonyl)piperidin-4-yl)zinc(II) iodide. Brown gum, MS: 489.4 [M+Na]$^+$.

Step 2: (R)-tert-Butyl 4-(4-(3-(3-methoxypyridazin-4-yl)-3-oxo-1-o-tolylpropyl)phenyl)-piperidine-1-carboxylate The title compound was produced in analogy to example 4, step 1 from (R)-tert-butyl 4-(4-(3-(methoxy(methyl)amino)-3-oxo-1-o-tolylpropyl)phenyl)piperidine-1-carboxylate and 3-methoxypyridazine. Orange gum, MS: 516.5 [M+H]$^+$.

Step 3: (R)-1-(3-Methoxypyridazin-4-yl)-3-(4-(piperidin-4-yl)phenyl)-3-o-tolylpropan-1-one To a solution of (R)-tert-butyl 4-(4-(3-(3-methoxypyridazin-4-yl)-3-oxo-1-o-tolylpropyl)-phenyl)piperidine-1-carboxylate (118 mg, 195 µmol) in 1,4-dioxane (4 mL) was added 37% aq. hydrochloric acid solution (0.32 mL, 3.9 mmol), then after 30 min the reaction mixture was partitioned between ethyl acetate and sat, aq. sodium hydrogencarbontesolution. The organic layer was washed with brine, dried over magnesium sulfate, filtered, and evaporated. Chromatography (SiO$_2$; gradient dichloromethane to dichloromethane/methanol/25% aq. ammonia solution 90:10:0.25) afforded the title compound (64 mg, 79%). Orange gum, MS: 416.2 [M+H]$^+$.

Step 4: (R)-1-(3-Methoxypyridazin-4-yl)-3-(4-(1-(methylsulfonyl)piperidin-4-yl)phenyl)-3-o-tolylpropan-1-one Methanesulfonyl chloride (35 mg, 0.31 mmol) was added at 0° C. to a solution of (R)-1-(3-methoxypyridazin-4-yl)-3-(4-(piperidin-4-yl)phenyl)-3-o-tolylpropan-1-one (64 mg, 154 µmol) and N,N-diisopropylethylamine (79.6 mg, 0.62 mmol) in dichlormethane (2.5 mL). The ice bath was removed, then after 1 h the reaction mixture was partitioned between sat. aq. ammonium chloride solution and ethyl acetate. The organic layer was washed with brine, dried over magnesium sulfate, filtered, and evaporated. Chromatography (SiO$_2$, heptane/ethyl acetate gradient) produced the title compound (60 mg, 79%). Light yellow gum, MS: 494.3 [M+H]$^+$.

Step 5: (R,E)-1-(3-Methoxypyridazin-4-yl)-3-(4-(1-(methylsulfonyl)piperidin-4-yl)phenyl)-3-o-tolylpropan-1-one oxime The title compound was produced in analogy to example 1, step 7 from (R)-1-(3-methoxypyridazin-4-yl)-3-(4-(1-(methylsulfonyl)piperidin-4-yl)phenyl)-3-o-tolylpropan-1-one. White solid, MS: 509.3 [M+H]$^+$.

Example 12

(R,E)-4-(1-(Hydroxyimino)-3-(4-(1-(methylsulfonyl)piperidin-4-yl)phenyl)-3-o-tolylpropyl)pyridazin-3(2H)-one

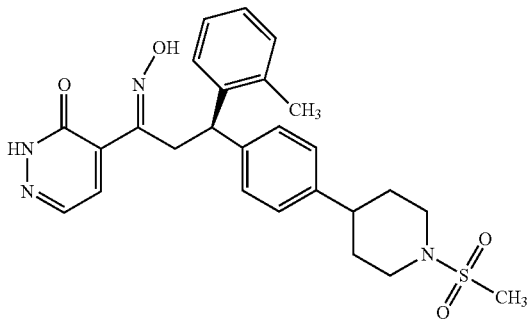 [SMILES: Cc1ccccc1[C@H](C/C(=N\O)c1ccn[nH]c1=O)c1ccc(C2CCN(S(C)(=O)=O)CC2)cc1]

Step 1: (R)-4-(3-(4-(1-(Methylsulfonyl)piperidin-4-yl)phenyl)-3-o-tolylpropanoyl)pyridazin-3(2H)-one To a solution of (R)-1-(3-methoxypyridazin-4-yl)-3-(4-(1-(methylsulfonyl)piperidin-4-yl)phenyl)-3-o-tolylpropan-1-one (example 12, step 4; 50 mg, 0.10 mmol) in 1,4-dioxane (1.5 mL) was added 37% aq. hydrochloric acid solution (0.17 mL, 2.0 mmol) and the resulting solution was heated at 80° C. for 2½ h, then after cooling partitioned between ethyl acetate and sat. aq. sodium hydrogencarbonate solution. The organic layer was washed with brine, dried over magnesium sulfate, filtered, and evaporated to produce the title compound (54 mg), which was directly used in the next step. Colorless gum, MS: 480.3 [M+H]⁺.

Step 2: (R,E)-4-(1-(Hydroxyimino)-3-(4-(1-(methylsulfonyl)piperidin-4-yl)phenyl)-3-o-tolylpropyl)pyridazin-3(2H)-one The title compound was produced in analogy to example 1, step 7 from (R)-4-(3-(4-(1-(methylsulfonyl)piperidin-4-yl)phenyl)-3-o-tolylpropanoyl)pyridazin-3(2H)-one. White solid, MS: 495.3 [M+H]⁺.

Example 13

(R,E)-4-(1-(Hydroxyimino)-3-(4-(1-(methylsulfonyl)piperidin-4-yl)phenyl)-3-o-tolylpropyl)-2-methylpyridazin-3(2H)-one

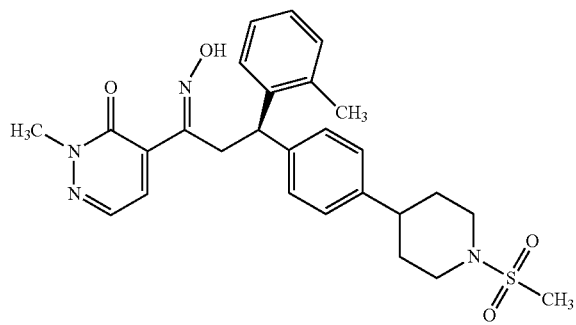

Step 1: (R)-2-Methyl-4-(3-(4-(1-(methylsulfonyl)piperidin-4-yl)phenyl)-3-o-tolylpropanoyl)pyridazin-3(2H)-one The title compound was produced in analogy to example 6, step 1 from 4-((R)-3-(4-(1-(methylsulfonyl)piperidin-4-yl)phenyl)-3-o-tolylpropanoyl)pyridazin-3(4H)-one (example 12, step 1) and iodomethane. White solid, MS: 494.4 [M+H]⁺.

Step 2: (R,E)-4-(1-(Hydroxyimino)-3-(4-(1-(methylsulfonyl)piperidin-4-yl)phenyl)-3-o-tolylpropyl)-2-methylpyridazin-3(2H)-one The title compound was produced in analogy to example 1, step 7 from (R)-2-methyl-4-(3-(4-(1-(methylsulfonyl)piperidin-4-yl)phenyl)-3-o-tolylpropanoyl)pyridazin-3(2H)-one. White solid, MS: 509.3 [M+H]⁺.

Example 14

(S,E)-6-(3-(4-Bromophenyl)-1-(hydroxyimino)-3-o-tolylpropyl)pyridazin-3(2H)-one

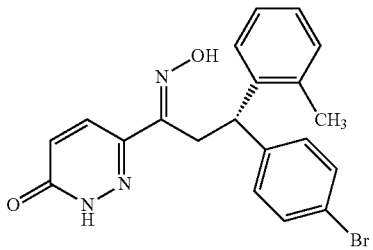 [SMILES: Cc1ccccc1[C@@H](C/C(=N\O)c1ccc(=O)[nH]n1)c1ccc(Br)cc1]

Step 1: (S)-6-(3-(4-Bromophenyl)-3-o-tolylpropanoyl)-3-methoxypyridazine 1-oxide The title compound was produced in analogy to example 7, step 1 from (S)-3-(4-bromo-phenyl)-N-methoxy-N-methyl-3-o-tolylpropanamide (example 1, step 5) and 3-methoxypyridazine-1-oxide. White foam, MS: 427.1 [M+H]⁺.

Step 2: (S)-3-(4-Bromophenyl)-1-(6-methoxypyridazin-3-yl)-3-o-tolylpropan-1-one

Water (0.2 mL) was added to a suspension of molybdenum (V) chloride (160 mg, 0.56 mmol) in THF (1 mL), then after 5 min zinc dust (60 mg, 0.92 mmol) was added portionwise, followed by (S)-6-(3-(4-bromophenyl)-3-o-tolylpropanoyl)-3-methoxypyridazine 1-oxide (100 mg, 0.23 mmol). The mixture was heated at reflux for 90 min, then partitioned between water and ethyl acetate. The organic layer was washed with brine, dried over magnesium sulfate, filtered, and evaporated in vacuo. Chromatography (SiO₂; heptane-ethyl acetate gradient) afforded the title compound (36 mg, 38%). Colorless gum, MS: 411.2 [M+H]⁺.

Step 3: (S)-6-(3-(4-Bromophenyl)-3-o-tolylpropanoyl)pyridazin-3(2H)-one

The title compound was produced in analogy to example 12, step 1 from (S)-3-(4-bromophenyl)-1-(6-methoxypyridazin-3-yl)-3-o-tolylpropan-1-one. White solid, MS: 397.1 [M+H]⁺.

Step 4: (S,E)-6-(3-(4-Bromophenyl)-1-(hydroxyimino)-3-o-tolylpropyl)pyridazin-3(2H)-one The title compound was produced in analogy to example 1, step 7 from (S)-6-(3-(4-bromophenyl)-3-o-tolylpropanoyl)pyridazin-3(2H)-one. White solid, MS: 412.1 [M+H]⁺.

The invention claimed is:
1. A compound according to formula I,

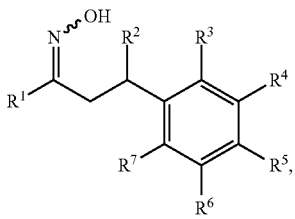

wherein
R¹ is a group selected from the group consisting of pyridazin-4-yl, 3-oxo-2,3-dihydro-pyridazin-4-yl "and 6-oxo-1,6-dihydropyridazin-3-yl, said group"being unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy and $C_{1-7}$-alkoxy-$C_{1-7}$-alkyl;

$R^2$ is selected from the group consisting of $C_{1-7}$-alkyl, $C_{3-7}$-cycloalkyl, $C_{2-7}$-alkenyl, halogen-$C_{1-7}$-alkyl, unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl, and heteroaryl, said heteroaryl being unsubstituted or substituted by $C_{1-7}$-alkyl or oxo, $R^3$ and $R^7$ are independently from each other selected from the group consisting of hydrogen, halogen and $C_{1-7}$-alkyl; and $R^4$, $R^5$ and $R^6$ are independently selected from the group consisting of hydrogen, halogen, halogen-$C_{1-7}$-alkyl, cyano, cyano-$C_{1-7}$-alkyl, $C_{1-7}$-alkyl, $C_{3-7}$-alkenyl, $C_{1-7}$-alkynyl, $C_{1-7}$-alkoxy, $C_{1-7}$-alkoxy-$C_{1-7}$ hydroxy, hydroxy-$C_{1-7}$-alkyl, hydroxy-$C_{3-7}$-alkenyl, hydroxy-$C_{3-7}$-alkynyl, hydroxy-$C_{1-7}$-alkoxy, carboxyl, carboxyl-$C_{1-7}$-alkyl, carboxyl-$C_{3-7}$-alkenyl, carboxyl-$C_{1-7}$-alkynyl, carboxyl-$C_{1-7}$-alkoxy, tetrazolyl, $C_{1-7}$-alkoxycarbonyl, $C_{1-7}$-alkylsulfonyl, $C_{1-7}$-alkylsulfonyloxy, $C_{1-7}$-alkylsulfonylamino, $C_{3-7}$-cycloalcylsulfonylamino, aminosulfonyl, ($C_{1-7}$-alkyl)-aminosulfonyl, di-($C_{1-7}$-alkyl)-aminosulfonyl, heterocyclylsulfonyl, $C_{1-7}$-alkyl-amino, di-($C_{1-7}$-alkyl)-amino, $C_{1-7}$-alkoxy-$C_{1-7}$-alkyl -amino, $C_{1-7}$-alkoxy-$C_{1-7}$-alkyl-$C_{1-7}$-alkyl-amino, $C_{1-7}$-alkoxy-halogen-$C_{1-7}$-alkyl-amino, hydroxy-$C_{1-7}$-alkyl-$C_{1-7}$-alkyl-amino, —NR—CHR$^A$—COOH, wherein R is hydrogen or lower alkyl and R$^A$ is the side chain of a natural amino acid, $C_{3-7}$-cycloalkyl-amino, wherein $C_{3-7}$-cycloalkyl is unsubstituted or substituted by hydroxy, hydroxy-$C_{1-7}$-alkyl or carboxyl, carboxyl-$C_{1-7}$-alkyl-aminocarbonyl, carboxyl-$C_{1-7}$-alkyl-($C_{1-7}$-alkyl) -aminocarbonyl, $C_{1-7}$-alkoxycarbonyl-$C_{1-7}$-alkyl-aminocarbonyl, $C_{1-7}$-alkyl-aminocarbonyl, di-($C_{1-7}$-alkyl)-aminocarbonyl, $C_{1-7}$-alkylsulfonyl-$C_{1-7}$-alkyl-aminocarbonyl, halogen-$C_{1-7}$-alkyl-aminocarbonyl, hydroxy-$C_{1-7}$-alkyl-aminocarbonyl, hydroxy-$C_{1-7}$-alkyl-$C_{1-7}$-alkyl-aminocarbonyl, halogen-hydroxy-$C_{1-7}$-alkyl -aminocarbonyl, $C_{1-7}$-alkoxy-$C_{1-7}$-alkyl-aminocarbonyl, $C_{3-7}$-cycloalkylaminocarbonyl, wherein $C_{3-7}$-cycloalkyl is unsubstituted or substituted by hydroxy, hydroxy-$C_{1-7}$-alkyl or carboxyl, heterocyclyl-aminocarbonyl, optionally substituted by $C_{1-7}$-alkyl or oxo, heterocyclyl-$C_{1-7}$-alkyl-aminocarbonyl, optionally substituted by $C_{1-7}$-alkyl or oxo, hydroxy-$C_{1-7}$-alkyl-aminocarbonyl-$C_{1-7}$-alkyl, $C_{1-7}$-alkoxycarbonyl-$C_{1-7}$-alkyl, di-($C_{1-7}$-alkoxycarbonyl)-$C_{1-7}$-alkyl, $C_{1-7}$-alkylcarbonylamino-$C_{1-7}$-alkylaminocarbonyl, $C_{1-7}$-alkylcarbonylamino, carboxyl-$C_{1-7}$-alkylcarbonylamino, $C_{1-7}$-alkoxycarbonyl-$C_{1-7}$-alkylcarbonylamino, $C_{3-7}$-cycloalkyl, wherein $C_{3-7}$-cycloalkyl is unsubstituted or substituted by hydroxy, hydroxy-$C_{1-7}$-alkyl or carboxyl, $C_{3-7}$-cycloalkyl-$C_{1-7}$-alkyl, wherein $C_{3-7}$-cycloalkyl is unsubstituted or substituted by hydroxy, hydroxy-$C_{1-7}$-alkyl or carboxyl, heterocyclyl, optionally substituted by $C_{1-7}$-alkyl, halogen, hydroxy, hydroxy-$C_{1-7}$-alkyl, $C_{1-7}$-alkoxy, oxo, carboxyl, carboxyl -$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl, heterocyclylcarbonyl, optionally substituted by $C_{1-7}$alkyl, halogen, hydroxy, hydroxy-$C_{1-7}$-alkyl, $C_{1-7}$-alkoxy, oxo, carboxyl, carboxyl -$C_{1-7}$-alkyl or $C_{1-7}$-alkylsulfonyl, heteroaryl, said heteroaryl being unsubstituted or substituted by $C_{1-7}$-alkyl, $C_{3-7}$-cycloalkyl, tetrahydropyranyl, carboxyl, carboxyl-$C_{1-7}$-alkyl, $C_{1-7}$-alkoxy-$C_{1-7}$-alkyl or $C_{1-7}$-alkoxycarbonyl, phenyloxy, wherein phenyl is unsubstituted or substituted by one to three groups selected from halogen or carboxyl, and phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl;

or a pharmaceutically acceptable salt thereof.

2. The compound according to claim 1, wherein $R^1$ is pyridazin-4-yl, said pyriclazin-4-yl being unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy and $C_{1-7}$-alkoxy-$C_{1-7}$-alkyl.

3. The compound according to claim 1, wherein $R^1$ is 6-oxo-1,6-dihydropyridazin-3-yl, said 6-oxo-1,6-dihydropyridazin-3-yl being unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy and $C_{1-7}$-alkoxy-$C_{1-7}$-alkyl.

4. The compound according to claim 1, wherein $R^1$ is 3-oxo-2,3-dihydro -pyridazin-4-yl, said 3-oxo-2,3-dihydropyridazin-4-yl being unsubstituted or substituted by one, two or three groups independently selected from the group consisting of $C_{1-7}$-alkyl, halogen, halogen-$C_{1-7}$-alkyl, hydroxy, hydroxy-$C_{1-7}$-alkyl, $C_{1-7}$-alkoxy and $C_{1-7}$-alkoxy-$C_{1-7}$-alkyl.

5. The compound according to claim 1, wherein $R^2$ is unsubstituted phenyl or phenyl substituted by one, two or three groups independently selected from the group consisting of $C_{1-7}$-alkyl, halogen, halogen-$C_{1-7}$-alkyl, halogen-$C_{1-7}$-alkoxy and $C_{1-7}$-alkylsulfonyl.

6. The compound according to claim 1, wherein $R^2$ is 2-methylphenyl.

7. The compound according to claim 1, wherein $R^3$ and $R^7$ are hydrogen.

8. The compound according to claim 1, wherein $R^5$ is selected from the group consisting of
- halogen, halogen-$C_{1-7}$-alkyl,
- cyano, cyano-$C_{1-7}$-alkyl,
- $C_{1-7}$-alkyl, $C_{3-7}$-alkenyl, $C_{1-7}$-alkynyl,
- $C_{1-7}$-alkoxy, $C_{1-7}$-alkoxy-$C_{1-7}$-alkyl,
- hydroxy, hydroxy-$C_{1-7}$-alkyl, hydroxy-$C_{3-7}$-alkenyl, hydroxy-$C_{3-7}$-alkynyl,
- hydroxy-$C_{1-7}$-alkoxy,
- carboxyl, carboxyl-$C_{1-7}$-alkyl, carboxyl-$C_{3-7}$-alkenyl, carboxyl-$C_{1-7}$-alkynyl,
- carboxyl-$C_{1-7}$-alkoxy,
- tetrazolyl,
- $C_{1-7}$-alkoxycarbonyl,
- $C_{1-7}$-alkylsulfonyl, $C_{1-7}$-alkylsulfonyloxy,
- $C_{1-7}$-alkylsulfonylamino, $C_{3-7}$-cycloalkylsulfonylamino,
- aminosulfonyl, ($C_{1-7}$-alkyl)-aminosulfonyl, di-($C_{1-7}$-alkyl)-aminosulfonyl,
- heterocyclylsulfonyl,
- $C_{1-7}$-alkyl-amino, di-($C_{1-7}$-alkyl)-amino, $C_{1-7}$-alkoxy-$C_{1-7}$-alkyl-amino,
- $C_{1-7}$-alkoxy-$C_{1-7}$-alkyl-$C_{1-7}$-alkyl-amino, $C_{1-7}$-alkoxy-halogen-$C_{1-7}$-alkyl-amino,
- hydroxy-$C_{1-7}$-alkyl-$C_{1-7}$-alkyl-amino,
- —NR—CHR$^4$—COOH, wherein R is hydrogen or lower alkyl and $R^4$ is the side chain of a natural amino acid,
- $C_{3-7}$-cycloalkyl-amino, wherein $C_{3-7}$-cycloalkyl is unsubstituted or substituted by hydroxy,
- hydroxy-$C_{1-7}$-alkyl or carboxyl,
- carboxyl-$C_{1-7}$-alkyl-aminocarbonyl, carboxyl-$C_{1-7}$-alkyl-($C_{1-7}$-alkyl)-aminocarbonyl,
- $C_{1-7}$-alkoxycarbonyl-$C_{1-7}$-alkyl-aminocarbonyl,
- $C_{1-7}$-alkyl-aminocarbonyl, di-($C_{1-7}$-alkyl)-aminocarbonyl,
- $C_{1-7}$-alkylsulfonyl-$C_{1-7}$-alkyl-aminocarbonyl,
- halogen-$C_{1-7}$-alkyl-aminocarbonyl, hydroxy-$C_{1-7}$-alkyl-aminocarbonyl,
- hydroxy-$C_{1-7}$-alkyl-$C_{1-7}$-alkyl-aminocarbonyl, halogen-hydroxy-$C_{1-7}$-alkyl-aminocarbonyl,
- $C_{1-7}$-alkoxy-$C_{1-7}$-alkyl-aminocarbonyl,
- $C_{3-7}$-cycloalkylaminocarbonyl, wherein $C_{3-7}$-cycloalcyl is unsubstituted or substituted by hydroxy, hydroxy-$C_{1-7}$-alkyl or carboxyl,
- heterocyclyl-aminocarbonyl, optionally substituted by $C_{1-7}$-alkyl or oxo,
- heterocyclyl-$C_{1-7}$-alkyl-aminocarbonyl, optionally substituted by $C_{1-7}$-alkyl or oxo,
- hydroxy-$C_{1-7}$-alkyl-aminocarbonyl-$C_{1-7}$-alkyl,
- $C_{1-7}$-alkoxycarbonyl-$C_{1-7}$-alkyl,
- di-($C_{1-7}$-alkoxycarbonyl)-$C_{1-7}$-alkyl,
- $C_{1-7}$-alkylcarbonylamino-$C_{1-7}$-alkylaminocarbonyl,
- $C_{1-7}$-alkylcarbonylamino, carboxyl-$C_{1-7}$-alkylcarbonylamino,
- $C_{1-7}$-alkoxycarbonyl-$C_{1-7}$-alkylcarbonylamino,
- $C_{3-7}$-cycloalkyl, wherein $C_{3-7}$-cycloalkyl is unsubstituted or substituted by hydroxy, hydroxyl -$C_{1-7}$-alkyl or carboxyl,
- $C_{3-7}$-cycloalkyl-$C_{1-7}$-alkyl, wherein $C_{3-7}$-cycloalkyl is unsubstituted or substituted by hydroxy,
- hydroxy-$C_{1-7}$-alkyl or carboxyl,
- heterocyclyl, optionally substituted by $C_{1-7}$-alkyl,
- halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl,
- carboxyl-$C_{1-7}$-alkyl-aminocarbonyl or hydroxysulfonyl-$C_{1-7}$-alkyl-aminocarbonyl,
- heterocyclylcarbonyl, optionally substituted by $C_{1-7}$-alkyl, halogen, hydroxy, hydroxy-$C_{1-7}$-alkyl, $C_{1-7}$-alkoxy, oxo, carboxyl, carboxyl -$C_{1-7}$-alkyl or $C_{1-7}$-alkylsulfonyl,
- heteroaryl, said heteroaryl being unsubstituted or substituted by $C_{1-7}$-alkyl, $C_{3-7}$-cycloalkyl,
- tetrahydropyranyl, carboxyl, carboxyl-$C_{1-7}$-alkyl, $C_{1-7}$-alkoxy-$C_{1-7}$-alkyl or $C_{1-7}$-alkoxycarbonyl,
- phenyloxy, wherein phenyl is unsubstituted or substituted by one to three groups selected from halogen or carboxyl, and
- phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl,
- $C_{1-7}$-alkoxy-carbonyl, tetrazolyl, carboxyl-$C_{1-7}$-alkyl-carbonylamino,
- $C_{1-7}$-alkoxy-carbonyl-$C_{1-7}$-alkyl-carbonylamino, $C_{1-7}$-alkylsulfonyl,
- $C_{1-7}$-alkyl-sulfonylamino, aminosulfonyl, $C_{1-7}$-alkyl-aminosulfonyl,
- di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl,
- $C_{1-7}$-alkoxycarbonyl-$C_{1-7}$-alkyl-carbonylamino-$C_{1-7}$-alkylsulfonyl,
- phenyl-$C_{1-7}$-alkyl-aminocarbonyl, tetrazolyl-aminocarbonyl,
- tetrazolyl-$C_{1-7}$-alkyl-aminocarbonyl and carboxyl-$C_{1-7}$-alkyl-aminocarbonyl;

and $R^4$ and $R^6$ are hydrogen.

9. The compound according to claim 1, wherein $R^5$ is selected from the group consisting of
- halogen, halogen-$C_{1-7}$-alkyl,
- cyano, cyano-$C_{1-7}$-alkyl,
- $C_{1-7}$-alkyl, $C_{3-7}$-alkenyl, $C_{1-7}$-alkynyl,
- $C_{1-7}$-alkoxy, $C_{1-7}$-alkoxy-$C_{1-7}$-alkyl,
- hydroxy, hydroxy-$C_{1-7}$-alkyl, hydroxy-$C_{3-7}$-alkenyl, hydroxy-$C_{3-7}$-alkynyl,
- hydroxy-$C_{1-7}$-alkoxy,
- carboxyl, carboxyl-$C_{1-7}$-alkyl, carboxyl-$C_{3-7}$-alkenyl, carboxyl-$C_{1-7}$-alkynyl, $C_{1-7}$-alkylsulfonyl,
- heterocyclyl, said heterocyclyl being unsubstituted or substituted by $C_{1-7}$-alkyl, halogen, hydroxy, hydroxy-$C_{1-7}$-alkyl, $C_{1-7}$-alkoxy, oxo, carboxyl, carboxyl-$C_{1-7}$-alkyl, $C_{1-7}$-alkoxycarbonyl, aminocarbonyl, $C_{1-7}$-alkylsulfonyl, aminosulfonyl, $C_{1-7}$-alkylcarbonyl, carboxyl-$C_{1-7}$-alkyl-aminocarbonyl or hydroxysulfonyl-$C_{1-7}$-alkyl-aminocarbonyl, and
- phenyl, said phenyl being unsubstituted or substituted by one to three groups selected from the group consisting of halogen, $C_{1-7}$-alkyl, hydroxy, hydroxy-$C_{1-7}$-alkyl, cyano, cyano-$C_{1-7}$-alkyl, amino, $C_{1-7}$-alkoxy, carboxyl, carboxyl-$C_{1-7}$-alkyl, $C_{1-7}$-alkoxy-carbonyl, tetrazolyl, carboxyl-$C_{1-7}$-alkyl-carbonylamino, $C_{1-7}$-alkoxy-carbonyl-$C_{1-7}$-alkyl-carbonylamino, $C_{1-7}$-alkylsulfonyl, $C_{1-7}$-alkyl-sulfonylamino, aminosulfonyl, $C_{1-7}$-alkyl-aminosulfonyl, di-($C_{1-7}$-alkyl)-aminosulfonyl, heterocyclylsulfonyl, $C_{1-7}$-alkoxycarbonyl-$C_{1-7}$-alkoxy, $C_{1-7}$-alkoxycarbonyl-$C_{1-7}$-alkyl-aminocarbonyl, carboxyl-$C_{1-7}$-alkyl-aminocarbonyl, $C_{1-7}$-alkoxycarbonyl-$C_{1-7}$-alkyl-carbonylamino-$C_{1-7}$-alkylsulfonyl, phenyl-$C_{1-7}$-alkyl-aminocarbonyl, tetrazolyl-aminocarbonyl, tetrazolyl-$C_{1-7}$-alkyl-aminocarbonyl and carboxyl-$C_{1-7}$-alkyl-aminocarbonyl;

and $R^4$ and $R^6$ are hydrogen.

10. The compound according to claim 1, wherein $R^5$ is selected from the group consisting of halogen, halogen-$C_{1-7}$-alkyl, carboxyl, carboxyl-$C_{1-7}$-alkyl, carboxyl-$C_{3-7}$-alkenyl, carboxyl-$C_{1-7}$-alkynyl, $C_{1-7}$-alkylsulfonyl, heterocyclyl, said heterocyclyl being unsubstituted or substituted by carboxyl or $C_{1-7}$-alkylsulfonyl, and phenyl, said phenyl being unsubstituted or substituted by carboxyl;

and $R^4$ and $R^6$ are hydrogen.

11. The compound according to claim 1, selected from the group consisting of (R,E)-3-(4-bromophenyl)-1-(pyridazin-4-yl)-3-o-tolylpropan-1-one oxime, (E)-4'-(3-(hydroxyimino)-3-(pyridazin-4-yl)-1-o -tolylpropyl)biphenyl-4-carboxylic acid, (E)-3-(4-(1-(methylsulfonyl)piperidin-4-yl)phenyl)-1-(pyridazin-4-yl)-3-o-tolylpropan-1-one oxime, (S,E)-3-(4-bromophenyl)-1-(3-methoxypyridazin-4-yl)-3-o -tolylpropan-1-one oxime, (S,E)-4-(3-(4-bromophenyl)-1-(hydroxyimino)-3-o -tolylpropyl)pyridazin-3(2H)-one, (S,E)-4-(3-(4-bromophenyl)-1-(hydroxyimino)-3-o-tolylpropyl)-2-methylpyridazin-3(2H)-one, (R,E)-6-(3-(4-bromophenyl)-1-(hydroxyimino)-3-o-tolylpropyl)-2-methylpyridazin-3(2H)-one, (R,E)-6-(1-(hydroxyimino)-3-(4-(1-(methylsulfonyl)piperidin-4-yl)phenyl)-3-o-tolylpropyl)-2-methylpyridazin-3(2H)-one, (R,E)-4'-(3-(hydroxyfinino)-3-(1-methyl-6-oxo-1,6-dihydropyridazin-3-yl)-1-o-tolylpropyl)biphenyl-4-carboxylic acid, (R,E)-6-(1-(hydroxylmino)-3-(4-(methylsulfonyl)phenyl)-3-o -tolylpropyl)-2-methylpridazin-3(2H)-one, (R,E)-1-(3-methoxypyridazin-4-yl)-3-(4-(1-(methylsulfonyl)piperidin-4-yl)phenyl)-3-o-tolylpropan-1-one oxime, (R,E)-4-(1-(hydroxyimino)-3-(4-(1-(methylsulfonyl)piperidin-4-yl)phenyl)-3-o-tolylpropyl)pyridazin-3(2H)-one, (R,E)-4-(1-(hydroxyiraino)-3-(4-(1-(methylsulfonyl)piperidin-4-yl)phenyl)-3-o-tolylpropyl)-2-methylpyridazin-3(2H)-one, (S,E)-6-(3-(4-bromophenyl)-1-(hydroxyintino)-3-o -tolylpropyl)pyridazin-3(2H)-one, and pharmaceutically acceptable salts thereof.

12. A pharmaceutical composition comprising the compound of claim 1 and a pharmaceutically acceptable carrier and/or adjuvant.

13. The compound of claim 1 wherein compound is 6-(1-(hydroxyimino)-3-(4-(1-(methylsulfonyl)piperidin-4-yl) phenyl)-3-o -tolylpropyl)-2-methylpyridazin-3(2H)-one, or a pharmaceutically acceptable salt thereof.

14. The compound of claim 1 wherein compound is 6(1-(hydroxyimino)-3-(4-(methylsulfonyl)phenyl)-3-o -tolylpropyl)-2-methylpyridazin-3(2H)-one, or a pharmaceutically acceptable salt thereof.

* * * * *